United States Patent
Frey et al.

(10) Patent No.: US 7,432,068 B2
(45) Date of Patent: *Oct. 7, 2008

(54) BIOSENSOR AND METHOD FOR DETECTING MACROMOLECULAR BIOPOLYMERS USING A BIOSENSOR

(75) Inventors: Alexander Frey, Munich (DE); Roland Thewes, Grobenzell (DE)

(73) Assignee: Siemens Aktiengesellschaft (DE)

( * ) Notice: Subject to any disclaimer, the term of this patent is extended or adjusted under 35 U.S.C. 154(b) by 642 days.

This patent is subject to a terminal disclaimer.

(21) Appl. No.: 10/239,007

(22) PCT Filed: Mar. 29, 2001

(86) PCT No.: PCT/DE01/01243

§ 371 (c)(1), (2), (4) Date: Mar. 19, 2003

(87) PCT Pub. No.: WO01/75437

PCT Pub. Date: Oct. 11, 2001

(65) Prior Publication Data

US 2003/0186263 A1   Oct. 2, 2003

(30) Foreign Application Priority Data

Mar. 30, 2000 (DE) ................. 100 15 818

(51) Int. Cl.
G01N 33/53 (2006.01)
(52) U.S. Cl. ...................................... 435/7.9
(58) Field of Classification Search ............ 435/4–7.95, 435/283.1–289.1, 783.1–789.1; 436/514–548; 422/50–73

See application file for complete search history.

(56) References Cited

U.S. PATENT DOCUMENTS

| | | | |
|---|---|---|---|
| 5,120,421 A | 6/1992 | Glass | |
| 5,670,031 A | 9/1997 | Hintsche et al. | |
| 5,865,972 A | 2/1999 | Buffle | |
| 5,874,046 A * | 2/1999 | Megerle | 422/68.1 |
| 6,133,046 A | 10/2000 | Clerc | |
| 6,221,586 B1 * | 4/2001 | Barton et al. | 435/6 |
| 2002/0028441 A1 | 3/2002 | Hintsche et al. | |
| 2004/0014054 A1 * | 1/2004 | Frey et al. | 435/6 |

FOREIGN PATENT DOCUMENTS

| | | |
|---|---|---|
| DE | 4318519 | 12/1994 |
| JP | 61-129560 | 6/1986 |
| JP | 10-010065 | 1/1998 |
| WO | WO 88/08528 | 11/1988 |
| WO | WO 93/22678 | 11/1993 |
| WO | WO 95/12808 | 5/1995 |
| WO | WO 96/01836 | 1/1996 |
| WO | WO 97/15827 | 5/1997 |
| WO | WO 97/19344 | 5/1997 |
| WO | WO 97/34140 | 9/1997 |
| WO | WO 98/29739 | 7/1998 |
| WO | WO 98/29740 | 7/1998 |
| WO | WO 99/24823 | 5/1999 |
| WO | WO 99/42558 | 8/1999 |
| WO | WO 99/67628 | 12/1999 |
| WO | WO 00/62048 | 10/2000 |

OTHER PUBLICATIONS

R. Hintsche et al., Microbiosensors Using Electrodes made in Si-Technology, Frontiers in Viosensorics, Fundamental Aspects, edited by F.W. Scheller et al., Birkhauser Verlag, Basle, pp. 267-283, 1997.
M. Paeschke et al., Voltammetric Multichannel Measurements Using Silicon Fabricated Microelectrode Arrays, Electroanalysis, vol. 7, No. 1, pp. 1-8, 1996.
P. Van Gerwen, Nanoscaled Interdigitated Electrode Arrays for Biochemical Sensors, IEEE, International Conference on Solid-State Sensors and Actuators, Chicago, pp. 907-910, Jun. 16-19, 1997.
C. Krause et al., Capacitive Detection of Surfactant Adsorption on Hydrophobized Gold Electrodes, Langmuir, vol. 12, No. 25, pp. 6059-6064, 1996.
V. Mirsky et al., Capacitive Monitoring of Protein Immobilization and Antigen-Antibody Reactions on Monomolecular Alkythiol Films on gold Electrodes, Biosensors & Bioelectronics, vol. 12, No. 9-10, pp. 977-989, 1997.
Hart, John P., Recent developments in the design and application of screen-printed electrochemical sensors for biomedical, environmental and industrial analysis. In: Trends in Analytical Chemistry, vol. 16, No. 1, pp. 89-103, 1997.

* cited by examiner

*Primary Examiner*—Ann Y Lam
(74) *Attorney, Agent, or Firm*—Altera Law Group LLC

(57) ABSTRACT

The invention relates to a first electrode that is provided with a holding area for holding probe molecules which can bind macro-molecular biopolymers. The first electrode and/or a second electrode is/are divided into a plurality of electrode segments that are electrically insulated from one another. The randomly selected electrode segments, independently from one another, can be electrically coupled in such a way that an effective electrode surface can be adjusted in the size thereof according to the selected electrode segments.

16 Claims, 17 Drawing Sheets

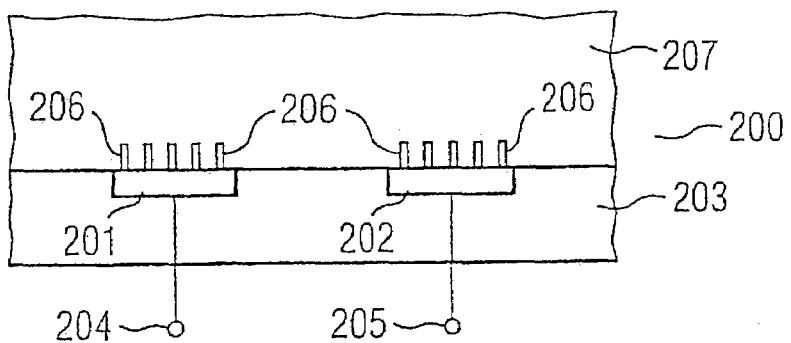
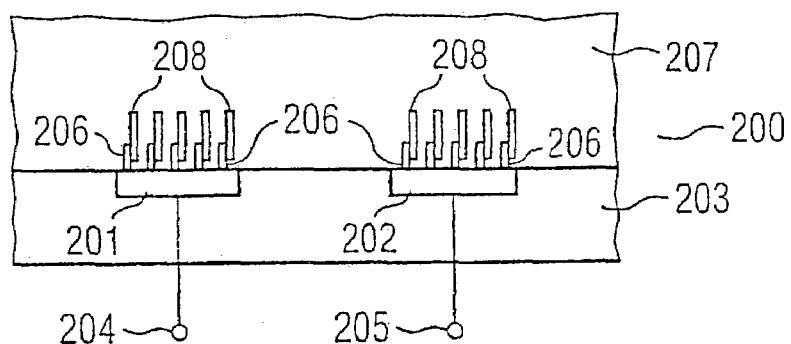
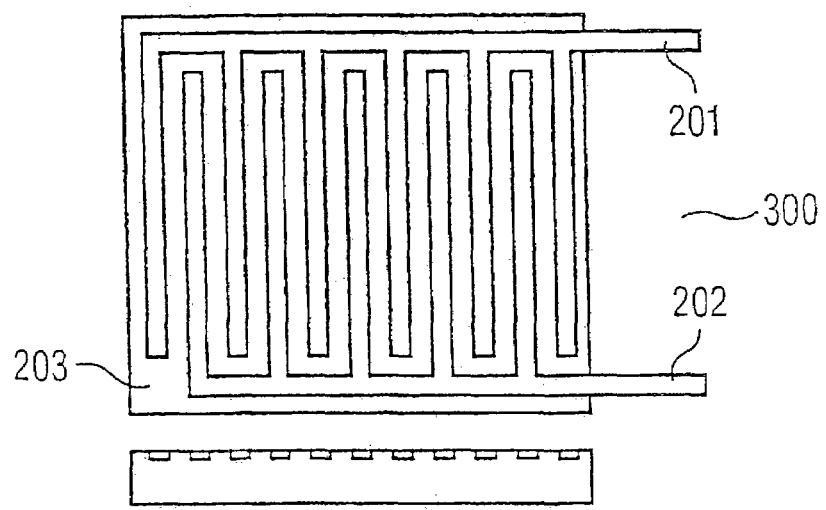

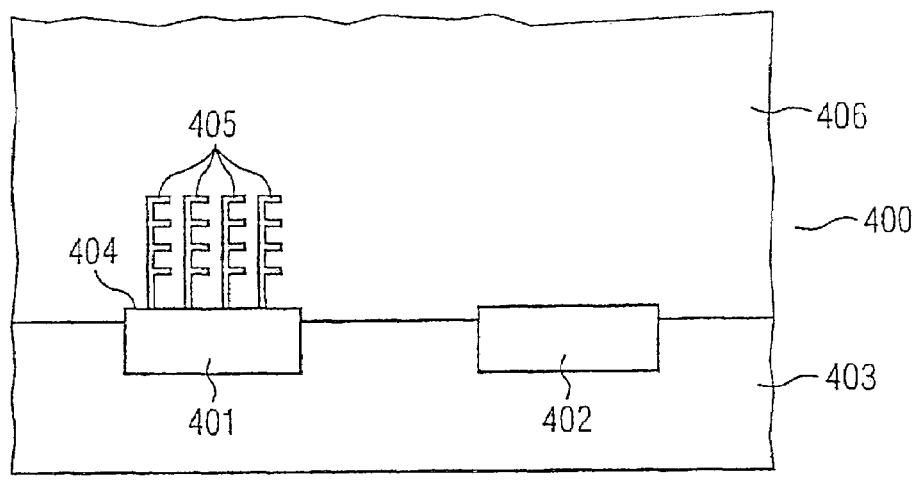
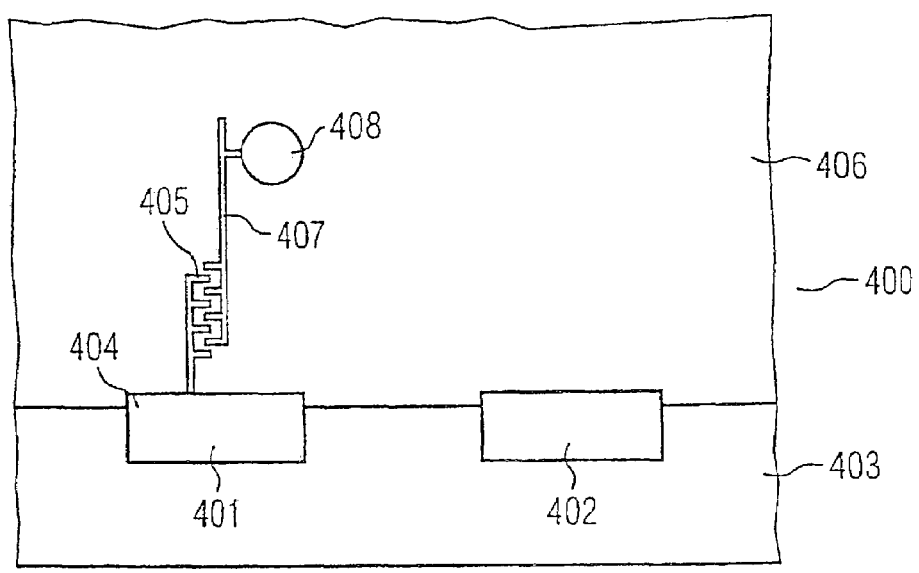

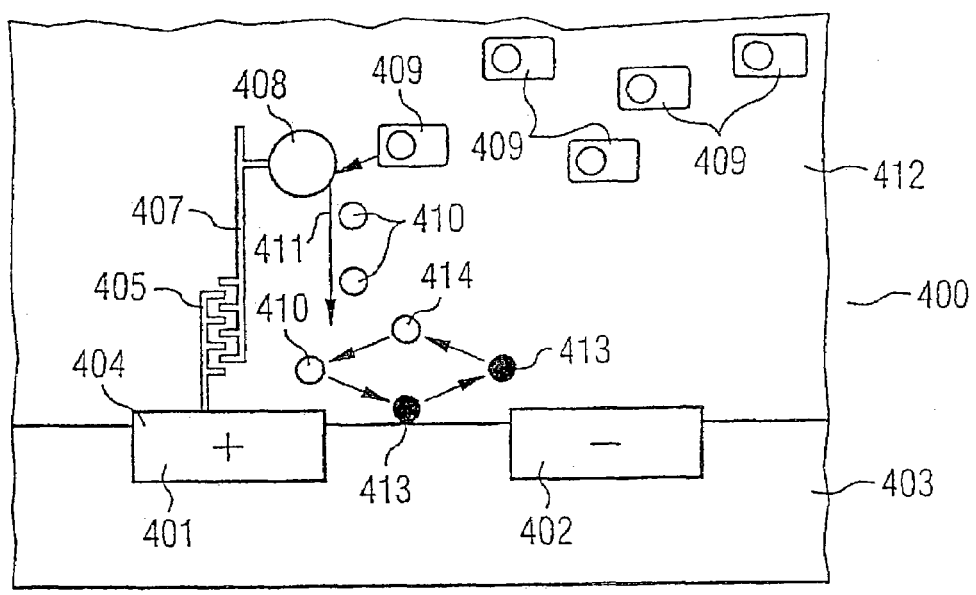
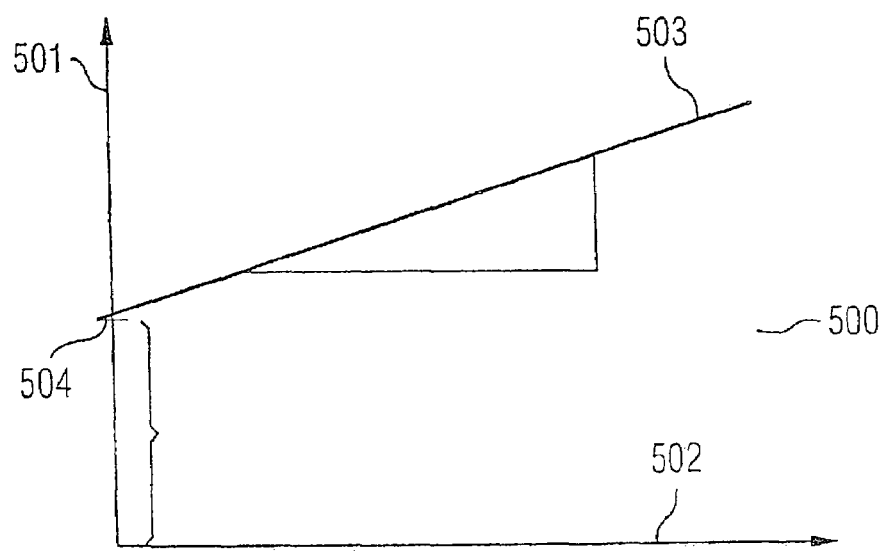

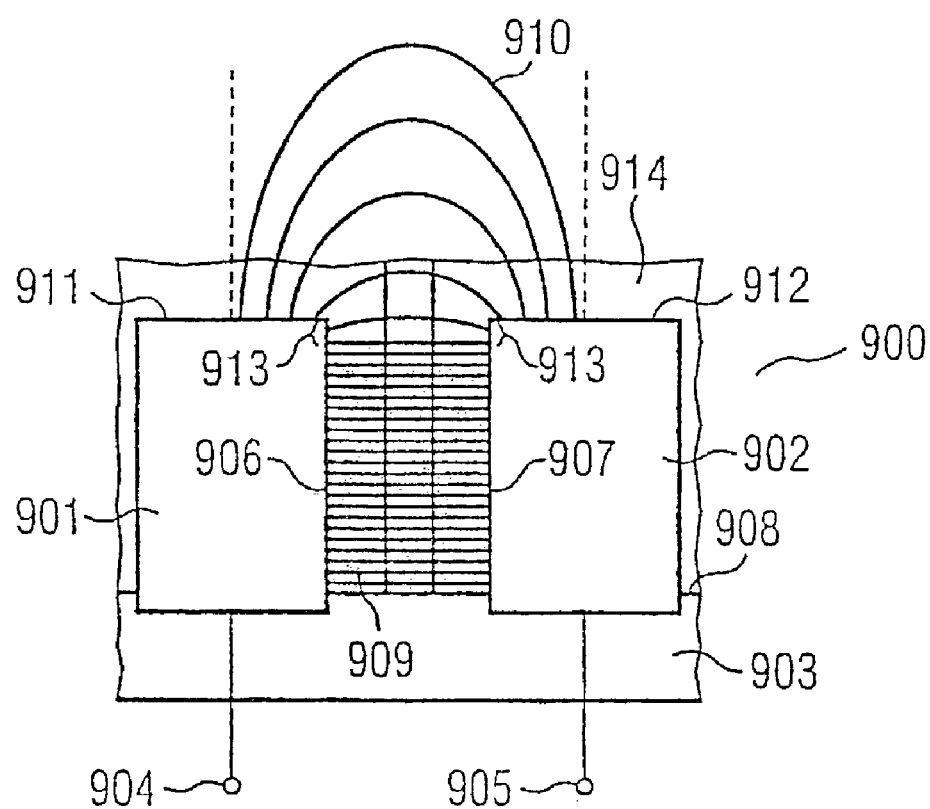

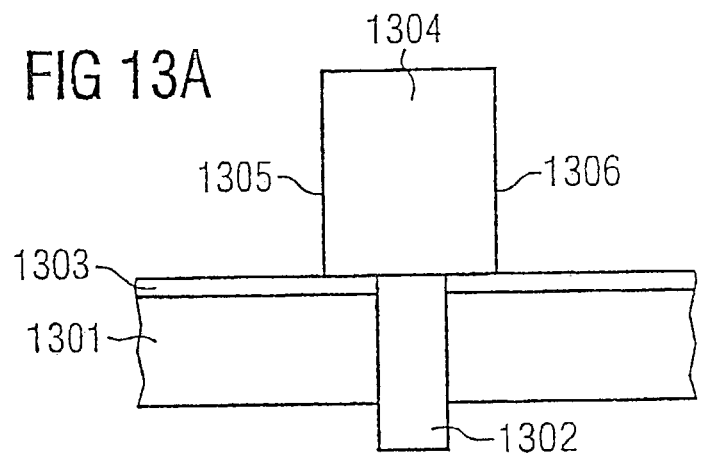
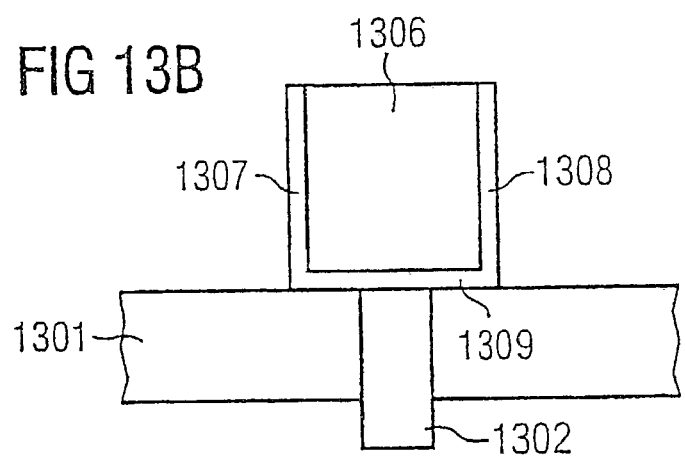
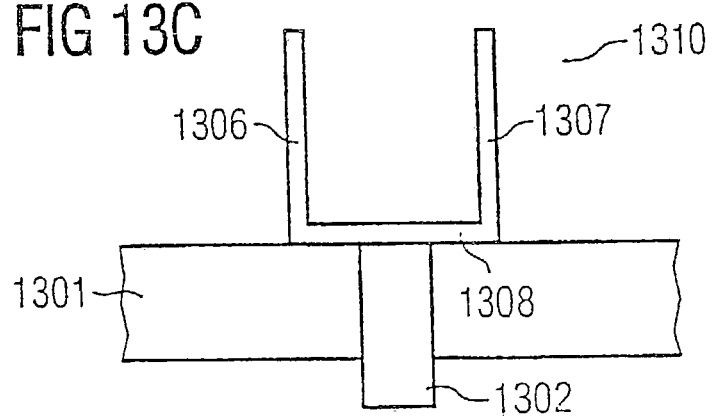

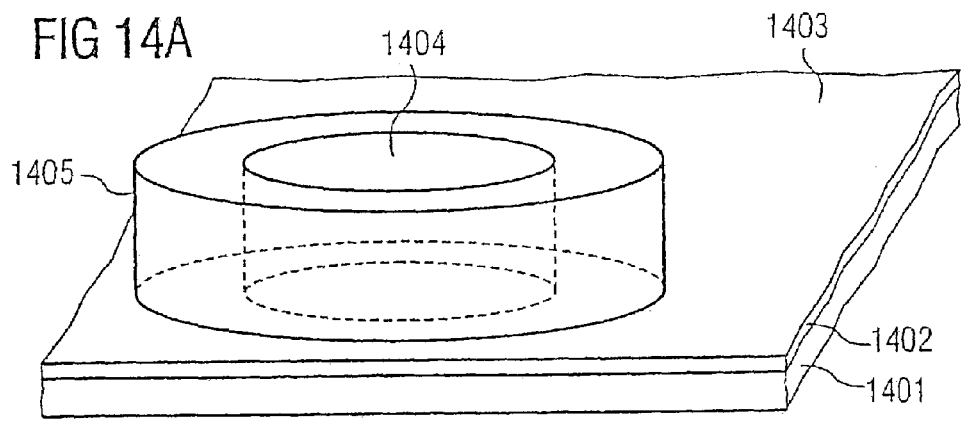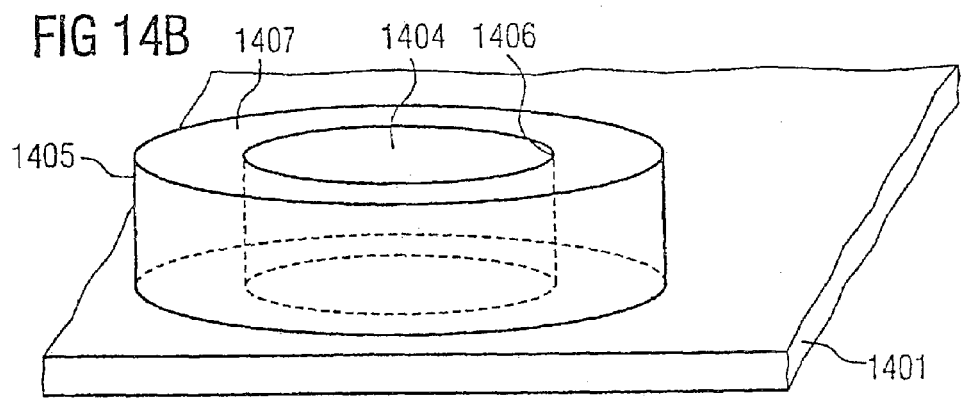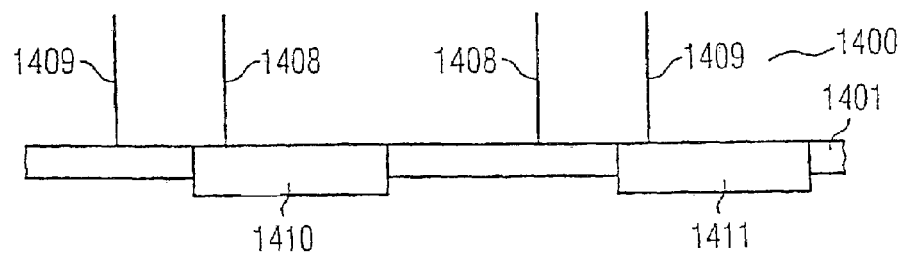

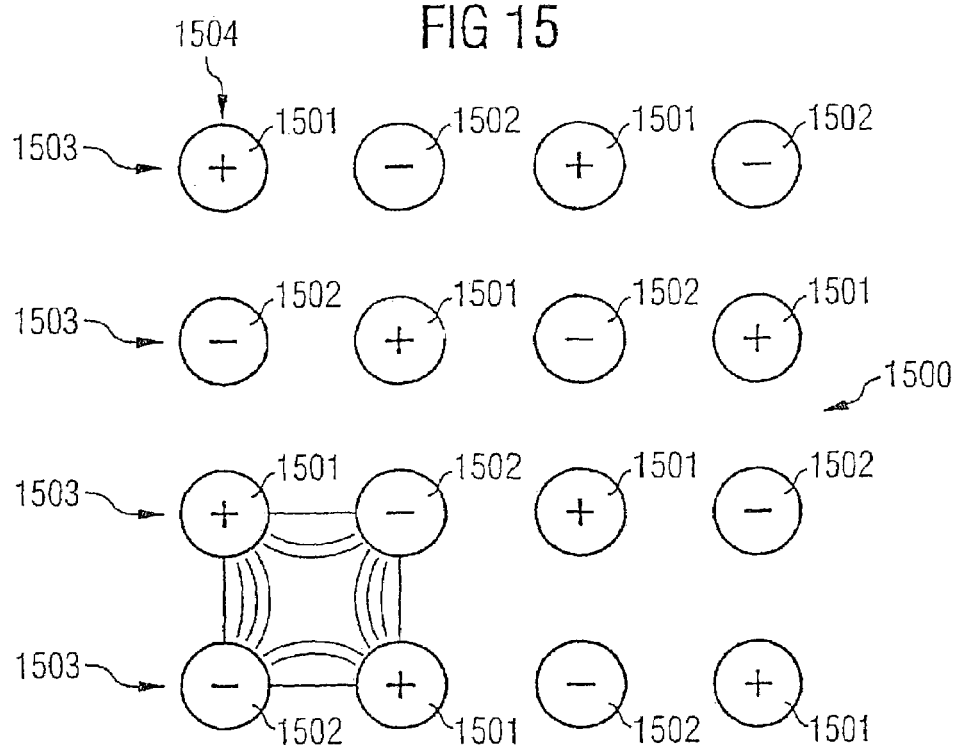
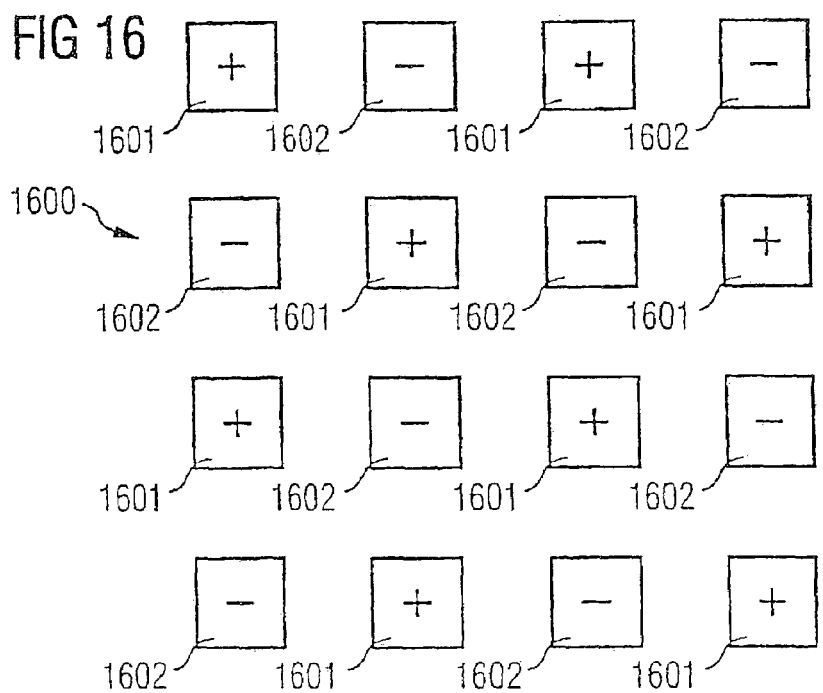

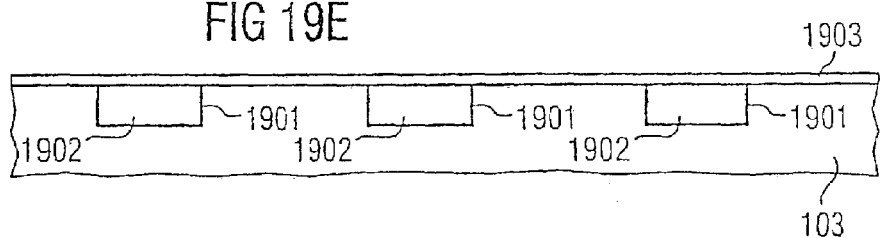
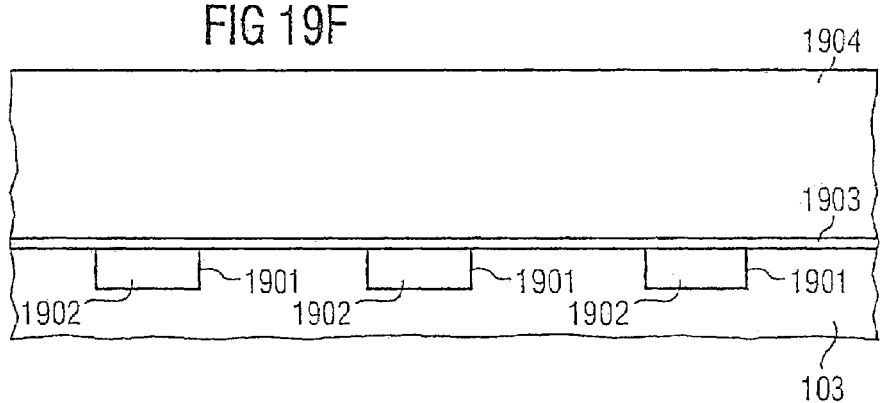
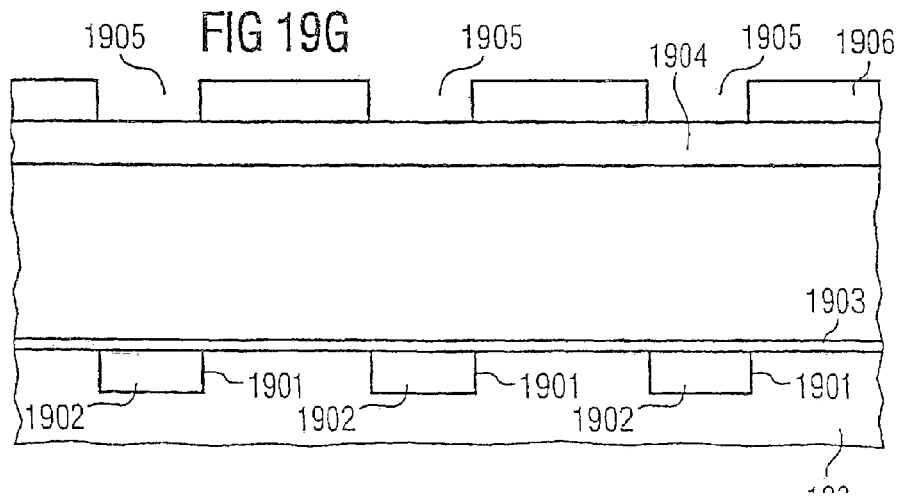

US 7,432,068 B2

BIOSENSOR AND METHOD FOR DETECTING MACROMOLECULAR BIOPOLYMERS USING A BIOSENSOR

BACKGROUND OF THE INVENTION

Field of the Invention

Description of the Related Prior Art

A biosensor chip of this type is known from [1].

FIG. 2a and FIG. 2b show such a biosensor chip, as described in [1]. The sensor 200 has two electrodes 201, 202 made of gold, which are embedded in an insulator layer 203 made of insulator material. Electrode terminals 204, 205, to which the electrical potential applied to the electrodes 201, 202 can be delivered, are connected to the electrodes 201, 202. The electrodes 201, 202 are arranged as planar electrodes. DNA probe molecules 206 are immobilized on each electrode 201, 202 (cf. FIG. 2a). The immobilization is carried out according to the so-called gold-sulfur coupling. The analyte to be analyzed, for example an electrolyte 207, is applied to the electrodes 201, 202.

If DNA strands 208 with a sequence which is complementary to the sequence of the DNA probe molecules 206 are contained in the electrolyte 207, then these DNA strands 208 hybridize with the DNA probe molecules 206 (cf. FIG. 2b).

Hybridization of a DNA probe molecule 206 and a DNA strand 208 takes place only if the sequences of the respective DNA probe molecule 206 and of the corresponding DNA strand 208 are complementary to one another. If this is not the case, then no hybridization takes place. A DNA probe molecule with a predetermined sequence is hence respectively able to bind, i.e. hybridize, only a particular DNA strand, namely the one with the complementary sequence in each case.

If hybridization takes place, then as can be seen from FIG. 2b, the value of the impedance between the electrodes 201 and 202 becomes modified. This modified impedance is determined by applying an AC voltage with an amplitude of approximately 50 mV to the electrode terminals 204, 205 and the resulting current by means of a connected measuring instrument (not shown).

In the event of hybridization, the capacitive component of the impedance between the electrodes 201, 202 is reduced. This is attributable to the fact that both the DNA probe molecules 206 and the DNA strands 208, which may hybridize with the DNA probe molecules 206 if appropriate, are non-conductive and therefore clearly shield the respective electrode 201, 202 electrically to a certain extent.

In order to improve the measurement accuracy, it is known from [4] to use a plurality of electrode pairs 201, 202 and to connect them in parallel, they being clearly arranged interdigitated with one another, so that a so-called interdigitated electrode 300 is obtained. The dimensioning of the electrodes and the distances between the electrodes are of the order of the length of the molecules to be detected, i.e. the DNA strand 208 or less, for example in the region of 200 nm and less.

Furthermore, basic principles of a reduction/oxidation recycling operation for detecting macromolecular biopolymers are known from [2] and [3]. The reduction/oxidation recycling operation, which is also referred to below as the redox recycling operation, is explained in more detail below with reference to FIG. 4a to FIG. 4c.

FIG. 4a shows a biosensor chip 400 having a first electrode 401 and a second electrode 402, which are applied to a substrate 403 as insulator layer.

A holding region, configured as holding layer 404, is applied to the first electrode 401 made from gold. The holding region is used to immobilize DNA probe molecules 405 on the first electrode 401.

There is no such holding region on the second electrode.

If DNA strands with a sequence which is complementary to the sequence of the immobilized DNA probe molecules 405 are to be recorded by means of the biosensor 400, the sensor 400 is brought into contact with a solution 406 which is to be analyzed, for example an electrolyte, in such a manner that any DNA strands which are present in the solution 406 which is to be analyzed and have the complementary sequence to the sequence of the DNA probe molecules 405 can hybridize.

FIG. 4b shows the situation in which the DNA strands 407 which are to be recorded are present in the solution 406 which is to be analyzed and have hybridized with the DNA probe molecules 405.

The DNA strands 407 in the solution which is to be analyzed are marked with an enzyme 408, allowing molecules which are described below to be cleaved into part-molecules.

There is usually a considerably greater number of DNA probe molecules 405 than the number of DNA strands 407 to be determined which are present in the solution 406 which is to be analyzed.

After the DNA strands 407 which may be present in the solution 406 which is to be analyzed, having the enzyme 408, have hybridized with the immobilized DNA probe molecules 407, the biosensor chip 400 is rinsed, with the result that the unhybridized DNA strands are removed and the solution 406 which is to be analyzed is cleaned off the biosensor chip 400.

An electrically uncharged substance which contains molecules which can be cleaved by the enzyme at the hybridized DNA strands 407 into a first part-molecule 410 with a negative electric charge and a second part-molecule with a positive electric charge is added to this rinsing solution which is used for rinsing or to a further solution which is supplied specifically for this purpose in a further phase.

As shown in FIG. 4c, the negatively charged first part-molecules 410 are attracted to the positively charged anode, i.e. to the first electrode 401, as indicated by the arrow 411 in FIG. 4c.

The negatively charged first part-molecules 410 are oxidized at the first electrode 401, which as anode has a positive electrical potential, and as oxidized part-molecules 413 are attracted to the negatively charged cathode, i.e. the second electrode 402, where they are reduced again. The reduced part-molecules 414 in turn migrate to the first electrode 401, i.e. to the anode.

In this way, an electric circuit current is generated, which is proportional to the number of charge carriers which are in each case generated by the enzymes 408.

The electrical parameter which is evaluated in this method is the change in the electric current $$\frac{dI}{dT}$$

as a function of time t, as diagrammatically illustrated in diagram 500 in FIG. 5.

FIG. 5 shows the function of the electric current 501 as a function of time 502. The resulting curve 503 has an offset current $I_{offset}$ 504 which is independent of the time profile.

The offset current $I_{offset}$ 504 is generated by parasitic components on account of imperfections in the biosensor 400.

A significant cause of the offset current $I_{offset}$ 504 is that the coverage of the first electrode 401 with DNA probe molecules 405 is not ideal, i.e. is not completely dense.

In the case of a completely dense coverage of the first electrode 401 with DNA probe molecules 405, only purely capacitive electrical coupling would result on account of what is known as the double-layer capacitance formed by the immobilized DNA probe molecules 405 between the first electrode 401 and the electrically conductive solution 406 which is to be analyzed.

However, the incomplete coverage leads to parasitic current paths between the first electrode 401 and the solution 406 which is to be analyzed, and these paths have, inter alia, ohmic components.

In order, however, to allow the oxidation/reduction process to take place, the coverage of the first electrode 401 with the DNA probe molecules 405 must not be complete, so that the electrically charged part-molecules, i.e. the negatively charged first part-molecules can be attracted to the first electrode 401 at all.

On the other hand, to achieve the highest possible sensitivity of a biosensor of this type, combined with low parasitic effects, the coverage of the first electrode 401 with DNA probe molecules 405 should be as dense as possible.

To achieve a high reproducibility of the measured values determined using a biosensor 400 of this type, both electrodes 401, 402 must always provide a sufficiently large surface area for the oxidation/reduction process as part of the redox recycling operation.

Therefore, in the biosensor according to the prior art, the result is a certain measurement unreliability in the detection of the DNA strands in a solution which is to be analyzed.

The term macromolecular biopolymers is to be understood as meaning, for example, proteins or peptides or also DNA strands of in each case a predetermined sequence.

If proteins or peptides are to be recorded as macromolecular biopolymers, the first molecules and the second molecules are ligands, for example active substances with a possible binding activity which bind the proteins or peptides which are to be recorded to the respective electrode on which the corresponding ligands are arranged.

Suitable ligands are enzyme agonists or enzyme antagonists, pharmaceuticals, sugars or antibodies or any molecule which has the ability to specifically bind proteins or peptides.

If DNA strands of a predetermined sequence are used as macromolecular biopolymers which are to be recorded by means of the biosensor, the biosensor can be used to hybridize DNA strands of a predetermined sequence to DNA probe molecules which have a complementary sequence to the sequence of the DNA strands, as molecules on the first electrode.

In the context of the present description, the term probe molecule is to be understood as meaning both a ligand and a DNA probe molecule.

The value $$\frac{dI}{dT}$$

is proportional to the electrode surface area of the electrodes used to record the measurement current. Therefore, given a constant width of the electrodes, the value $$\frac{dI}{dT}$$

is proportional to the longitudinal extent of the electrodes used, for example, in the case of the first electrode 201 and the second electrode 202, to their length perpendicular to the plane of the drawing in FIG. 2a and FIG. 2b.

If a plurality of electrodes are connected in parallel, for example in the known interdigitated electrode arrangement, the change in the measurement current $$\frac{dI}{dT}$$

is also proportional to the number of electrodes which are in each case connected in parallel.

However, the value of the change in the measurement current $$\frac{dI}{dT}$$

may, on account of various influences, have a range of values which fluctuates very considerably, in particular for different solutions which are to be analyzed.

The cause of the considerable fluctuations may on the one hand be the dynamic range required for DNA strands of a predetermined sequence which are to be detected, in order to allow them to be recorded at all.

On the other hand, however, it is also possible that different macromolecular biopolymers of different types which are to be detected lead to very different ranges of values for the resulting measurement signal, i.e. in particular the measurement current and its time change $$\frac{dI}{dT},$$

which in turn leads to a widening in the overall dynamic range required for a predetermined electrode configuration with subsequent integrated measurement electronics, i.e. with a subsequent integrated measurement circuit.

The measurement electronics, which records and processes further the time change between the electrodes, i.e. between anode and cathode, has to function reliably and accurately within the required ranges of values. The demands imposed on the wide dynamic range of a circuit of this type lead to the measurement electronics being expensive and complicated in order to provide the required dynamic range.

The situation in which the electrical measurement signals which are to be detected have to be measurable over a wide dynamic range may also occur in other methods, as are known, for example, from [4], [5], [6], [7] and [8].

In these cases too, extreme demands may be imposed on the measurement electronics, i.e. the evaluation circuit, in terms of its dynamics. Particularly during the circuit design, the imperfections of the components used, i.e. a noise, the variation in the parameters of the components, are taken into account in a form which is such that a working point at which these imperfections have the minimum possible influence on the quality of the measurement result, is selected for these components in the circuit which is designed. If a circuit is to be operated over a wide dynamic range, it becomes increasingly difficult and expensive to maintain an optimum working point for all ranges.

SUMMARY OF THE INVENTION

Therefore, the invention is based on the problem of providing a biosensor in which, for downstream measurement electronics, the demands relating to the recording of measurement signals, the value of which may fluctuate considerably, are reduced.

The problem is solved by the biosensor and the method for detecting macromolecular biopolymers using a biosensor having the features described in the independent patent claims.

A biosensor has a first electrode, which has a holding region for holding probe molecules which can bind macromolecular biopolymers. Furthermore, the biosensor has a second electrode. The first electrode and/or the second electrode are divided into a plurality of electrode segments which are electrically insulated from one another, it being possible for electrode segments, which are selected as desired, to be electrically coupled independently of one another, so that the size of an effective electrode face can be adjusted as a function of the electrode segments selected.

The term macromolecular biopolymers is to be understood as meaning, by way of example, proteins or peptides or DNA strands of in each case a predetermined sequence.

If proteins or peptides are to be recorded as macromolecular biopolymers, the first molecules and the second molecules are ligands, for example active substances with a possible binding activity, which bind the proteins or peptides which are to be recorded to the respective electrode on which the corresponding ligands are arranged.

Suitable ligands are enzyme agonists or enzyme antagonists, pharmaceuticals, sugars or antibodies or any molecule which has the ability to specifically bind proteins or peptides.

If the macromolecular biopolymers used are DNA strands of a predetermined sequence which are to be recorded by means of the biosensor, the biosensor can be used to hybridize DNA strands of a predetermined sequence to DNA probe molecules having the sequence which is complementary to the sequence of the DNA strands, as molecules on the first electrodes.

In the context of the present description, the term probe molecule is to be understood as meaning both a ligand and a DNA probe molecule.

A sensor of this type is used as part of a method for detecting macromolecular biopolymers.

In this method, a solution which is to be analyzed is brought into contact with the biosensor, it being possible for the solution to contain the macromolecular biopolymers which are to be recorded. Macromolecular biopolymers which are present in the solution which is to be analyzed are bound to probe molecules immobilized on the first electrode, the bound macromolecular biopolymers being marked with an enzyme.

The biosensor is rinsed with a rinsing solution, so that the solution which is to be analyzed, as well as any unhybridized, i.e. unbound macromolecular biopolymers are removed from the biosensor, i.e. in particular from the electrodes.

A further solution containing molecules which can be cleaved by the enzyme is brought into contact with the biosensor. In each case one cleavable molecule is cleaved by means of the enzyme into a first part-molecule having a first charge and a second part-molecule having a second charge. The first part-molecule is oxidized or reduced at one of the electrodes and is correspondingly reduced or oxidized at the other electrode, with the result that a measurement current is generated.

The measurement current is the circuit current which is described above and is known in accordance with the prior art as part of the reduction/oxidation recycling operation.

Electrode segments are selected and electrically coupled to one another as a function of the measurement current, so that the size of the effective electrode face of the biosensor is adjusted as a function of the electrode segments selected. The macromolecular biopolymers are detected as a function of the measurement current detected.

In other words, this means that it is possible both to determine whether the macromolecular biopolymers which are to be recorded were in fact present in the solution to be analyzed. It is even possible, on account of the accuracy of the measurement method, to make a statement regarding the number of bound macromolecular biopolymers in the solution to be analyzed which have been bound to the probe molecules.

This is possible since, if a large number of DNA strands which have been marked with the enzyme are hybridized with immobilized DNA probe molecules in a predetermined region of the first electrode, a correspondingly large number of these enzymes are concentrated at this region, and the rate at which the current circuit generated increases is higher than in a region where fewer DNA strands which have been marked with the active enzyme are hybridized.

By comparing the rates of increase between various regions of electrodes of a biosensor, it is in this way possible to determine not only whether DNA strands are hybridizing in the solution which is to be analyzed with the DNA probe molecules of a predetermined sequence, but also how well, i.e. with what level of efficiency, this hybridization takes place compared to other DNA probe molecules.

In other words, qualitative and quantitative information concerning the DNA content, and in general concerning the content of macromolecular biopolymers in the solution to be analyzed, can be determined by means of the biosensor.

The biosensor may include electrical switches, of which in each case one switch is coupled to an associated electrode segment in such a manner that in a first switch position of a switch, the associated electrode segment is selected and the electrode segment is electrically coupled to a common connection. In a second switch position, the associated electrode segment is not selected. In this case, the associated electrode segment is coupled to a predetermined electric potential.

Measurement electronics for measuring an electrical signal provided by the selected electrode segments may be coupled to the biosensor, the input of the measurement electronics being electrically coupled to the selected electrode segments. The measurement electronics may be integrated on the same chip as the electrodes of the biosensor or may also be arranged outside the biosensor.

Furthermore, a switch control unit, which is coupled to the measurement electronics, may be provided for controlling the switches, and in general terms for controlling the selection units.

According to one configuration of the invention, the switch control unit is designed in such a manner that the switches can be controlled as a function of the electrical signal recorded by the measurement electronics.

The second electrode may be divided into a plurality of electrode segments which are electrically insulated from one another, it being possible for the electrode segments of the second electrode which are selected as desired to be electrically coupled independently of one another, so that the size of the effective electrode face can be adjusted as a function of the electrode segments selected. According to this refinement, the electrode segment which is not selected is coupled to the predetermined electrical potential in such a manner that a reduction/oxidation recycling operation can take place at the electrodes.

Furthermore, a third electrode may be provided in the biosensor, the second electrode and the third electrode being designed differently than the first electrode and in such a manner that the reduction/oxidation process takes place as part of a reduction/oxidation recycling operation at the second electrode and at the third electrode.

This can be achieved, for example, if the first electrode has a first electrical potential, the second electrode has a second electrical potential, and the third electrode has a third electrical potential. The third electrical potential is selected in such a manner that during the reduction/oxidation recycling operation, the reduction or oxidation takes place substantially only at the second electrode and at the third electrode.

By way of example, this choice may be made in such a manner that the third electrical potential is selected to be greater than the first electrical potential, and that the first electrical potential, which is applied to the first electrode, is greater than the second electrical potential, which is applied to the second electrode.

The holding region of the first electrode may be coated with a material which can immobilize probe molecules.

Furthermore, the holding region of the first electrode may be designed to hold ligands to which peptides or proteins can be bound.

Furthermore, the holding region of the first electrode may be designed to hold DNA probe molecules to which DNA molecules can be bound.

The first holding region may contain at least one of the following materials:
 hydroxyl radicals,
 epoxy radicals,
 amine radicals,
 acetoxy radicals,
 isocyanate radicals,
 succinimidyl ester radicals,
 thiol radicals,
 gold,
 silver,
 platinum,
 titanium.

Examples of enzymes which can be used include
 a-galactosidase,
 b-galactosidase,
 b-glucosidase,
 a-mannosidase,
 alkaline phosphatase,
 acidic phosphatase,
 oligosaccharide dehydrogenase,
 glucose dehydrogenase,
 laccase,
 tyrosinase,
 or enzymes of related types.

It should be noted that low-molecular weight enzymes are able to ensure the highest conversion efficiency and therefore also the highest sensitivity.

Therefore, the further solution contains molecules which can be cleaved by the enzyme into a first part-molecule with a negative electric charge and into a second part-molecule with a positive electric charge.

By way of example, above all
 p-aminophenyl hexopyranosides,
 p-aminophenyl phosphates,
 p-nitrophenyl hexopyranosides,
 p-nitrophenyl phosphates, or
 suitable derivatives of
  a) diamines,
  b) catecholamines,
  c) $Fe(CN)^{4-}_6$,
  d) ferrocene,
  e) dicarboxylic acid,
  f) ferrocenelysine,
  g) osmium bipyridyl NH, or
  h) PEG-ferrocene2,
can be used as the cleavable molecule.

An exemplary embodiment of the invention is illustrated in the figures and explained in more detail below.

BRIEF DESCRIPTION OF THE DRAWINGS

In the drawing.

FIGS. 2a and 2b show a sketch of two planar electrodes, by means of which the existence of DNA strands which are to be recorded in an electrolyte (FIG. 2a) or their nonexistence (FIG. 2b) can be detected;

FIG. 3 shows interdigitated electrodes according to the prior art.

FIGS. 4a to 4c show sketches of a biosensor in accordance with the prior art, on the basis of which individual states as part of the redox recycling operation are explained;

FIG. 5 shows a functional curve of a circuit current in accordance with the prior art as part of a redox recycling operation;

FIG. 9 shows a biosensor in accordance with an exemplary embodiment of the invention;

FIGS. 13a to 13c show cross-sectional views through a biosensor during individual method steps of the method for producing an electrode of the biosensor in accordance with a further exemplary embodiment of the invention;

FIGS. 14a to 14c respectively show a cross section through a biosensor at various times during the production method in accordance with a further exemplary embodiment of the invention;

FIG. 15 shows a plan view of a biosensor array according to an exemplary embodiment of the invention with cylindrical electrodes;

FIG. 16 shows a plan view of a biosensor array in accordance with an exemplary embodiment of the invention with cuboidal electrodes;

FIGS. 19a to 19g show cross-sectional views through a biosensor during individual method stages of a production method according to a further exemplary embodiment of the invention.

DESCRIPTION OF THE PREFERRED EMBODIMENTS

Figure 1A:
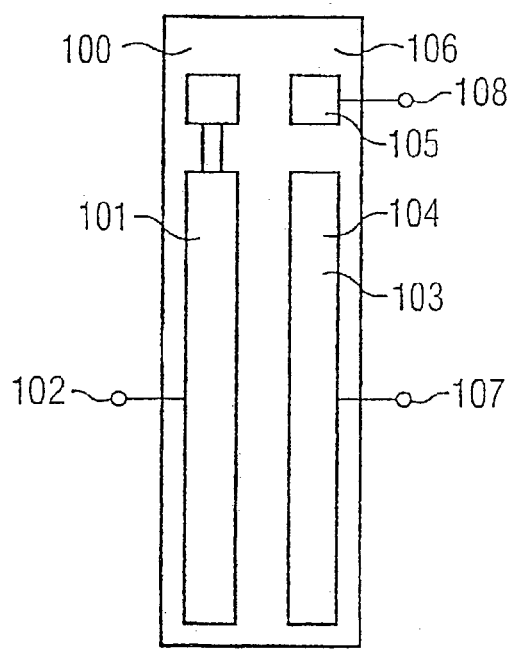
FIGS. 1a to 1c illustrate various electrode arrangements in plan view, FIG. 1A showing a sketch of an electrode arrangement in accordance with a first exemplary embodiment of the invention, FIG. 1b showing an electrode arrangement in accordance with a second exemplary embodiment of the invention and FIG. 1c showing an interdigitated electrode arrangement in accordance with an exemplary embodiment of the invention.

FIG. 1a shows a biosensor 100 in accordance with a first exemplary embodiment of the invention.

The biosensor 100 has a first electrode 101 which is electrically coupled to a first electrical connection 102.

The second electrode 103 of the biosensor has a first electrode segment 104 and a second electrode segment 105.

The first electrode 101 and the second electrode 103 are made from gold.

The two electrode segments 104, 105 of the second electrode 103 are electrically insulated from one another by means of an insulator layer 106, by means of which, furthermore, the first electrode 101 and the second electrode 103 are electrically insulated from one another.

The first electrode segment 104 is electrically coupled to a second electrical connection 107, and the second electrode segment 105 of the second electrode 103 is electrically coupled to a third electrical connection 108.

The first electrode segment 104 and the second electrode segment 105 can optionally be electrically coupled to one another or electrically insulated from one another.

Obviously, the second electrode 103 as a whole is generally divided into any desired number of electrode segments 104, 105, so that the electrode is divided into independent electrode segments which are electrically insulated from one another.

The independent selection and electrical coupling of the individual electrode segments 104, 105 of the second electrode 103 allows the size of the effective electrode face which is selected for recording the measurement signal to be varied and controlled in a very simple and flexible manner.

In this way, it evidently becomes possible for the entire sensor, i.e. the entire second electrode 103, or only a partial region, i.e. one or more electrode segments of the second electrode 103, to be electrically coupled to the measurement electrode, for example as a function of the level of the measurement current.

Therefore, it is possible to ensure that the entire circuit is adapted so as to record the measurement current in the available dynamic range of the measurement electronics.

In particular, it becomes possible in general terms to ensure that the measurement range is mapped onto a dynamic range of the circuit which is considerably narrower than in the prior art as a result of the circuit operating optimally in accordance with predetermined criteria.

On account of the proportionality in the change in the measurement current over the course of time to the effective electrode surface area as explained above, variable tapping of the measurement signal from the second electrode 103 is therefore possible.

Figure 1B:
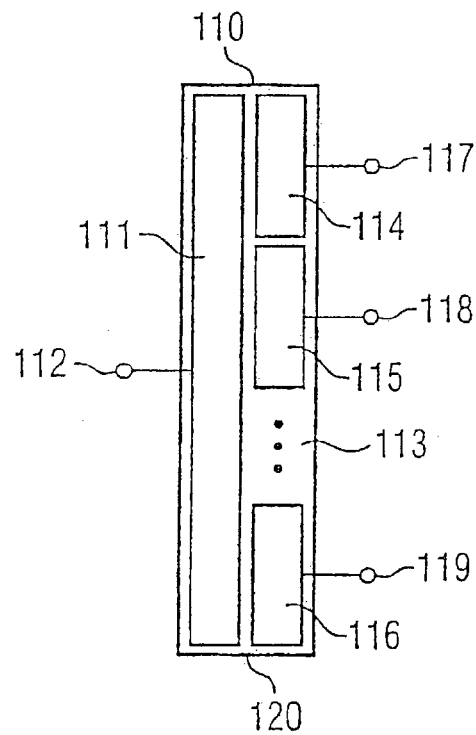

FIG. 1b shows a more general embodiment of the biosensor 100 illustrated in FIG. 1a.

In the case of the biosensor 110 illustrated in FIG. 1b, in addition to the first electrode 111 having a first electrical connection 112, n electrode segments of a second electrode 113 are provided.

Once again, the first electrode 111 and the second electrode 113 contain gold.

Each of the n electrode segments 114, 115, 116 is electrically coupled to an electrical connection 117, 118, 119. The electrode segments 114, 115, 116 are electrically insulated from one another and from the first electrode 111 by means of an insulator layer 120.

The electrical connections 117, 118, 119 can be electrically coupled to one another in any desired way which can be selected freely.

In accordance with predeterminable sizes of the individual electrode segments 114, 115, 116, a measurement current which is proportional to the electrode surface area of the electrode segments selected can be brought together at a common connection which is described in more detail below and can in this way be fed to measurement electronics.

According to the exemplary embodiment which is illustrated in FIG. 1b, a length ratio of the first electrode to the overall length of all the electrode segments 114, 115, 116 of the second electrode 113 of 1:9 was selected, i.e. according to this exemplary embodiment the second electrode 113 has nine electrode segments 114, 115, 116, (n=9), where the sum of the electrode surface area of the electrode segments 114, 115, 116 of the second electrode 113 corresponds to the electrode surface area of the first electrode 111.

This means that when all the electrode segments 114, 115, 116 of the second electrode 113 are connected together, 100% of the measurement current which is generated and is produced in accordance with the reduction/oxidation recycling operation illustrated in FIG. 4a to FIG. 4c is tapped at measurement electronics for evaluating the measurement current or its temporal differentiation.

The configuration described below relates to all the exemplary embodiments of the invention.

On the first electrodes there are holding regions for immobilizing DNA probe molecules. In the holding regions, DNA probe molecules are immobilized in accordance with the gold-sulfur coupling.

In a first step, a solution which is to be analyzed and in which the DNA strands which are to be recorded and have a sequence which is complementary to the sequence of the DNA probe molecules, is contained, is brought into contact with at least the first electrode.

If the solution which is to be analyzed contains DNA strands with a sequence which is complementary to the sequence of the DNA probe molecules, these strands hybridize with the DNA probe molecules.

In a further step, a rinsing solution is applied to the biosensor, in particular to the first electrode, with the result that the solution which is to be analyzed and unhybridized DNA strands, and in general terms unbound macromolecular biopolymers, are removed from the biosensor, in particular from the first electrode.

The DNA strands are marked with an enzyme.

The following substances are used as the enzyme:

By way of example, the enzyme used may be
- a-galactosidase,
- b-galactosidase,
- b-glucosidase,
- a-mannosidase,
- alkaline phosphatase,
- acidic phosphatase,
- oligosaccharide dehydrogenase,
- glucose dehydrogenase,
- laccase,
- tyrosinase,
- or enzymes of related types.

It should be noted that low-molecular weight enzymes are able to ensure the highest conversion efficiency and therefore also the highest sensitivity.

With the enzymes, it is possible to cleave molecules which are brought into contact with the first electrode in a further solution into a first part-molecule of a first electric charge and into a second part-molecule of a second electrode charge.

According to these exemplary embodiments, the following molecules are used as cleavable molecules:
- p-aminophenyl hexopyranosides,
- p-aminophenyl phosphates,
- p-nitrophenyl hexopyranosides,
- p-nitrophenyl phosphates, or
- suitable derivatives of
  a) diamines,
  b) catecholamines,
  c) $Fe(CN)_6^{4-}$,
  d) ferrocene,
  e) dicarboxylic acid,
  f) ferrocenelysine,
  g) osmium bipyridyl NH, or
  h) PEG-ferrocene2.

A first potential V1 is applied to the first electrode, and a second electrical potential V2 is applied to the second electrode. The first electrical potential V1 is greater than the second electrical potential V2.

Therefore, in accordance with the reduction/oxidation recycling operation illustrated in FIG. 4a to FIG. 4c, charge carriers are generated in the further solution, with the result that a circuit current, which is referred to below as the measurement current, is generated.

Figure 1C:
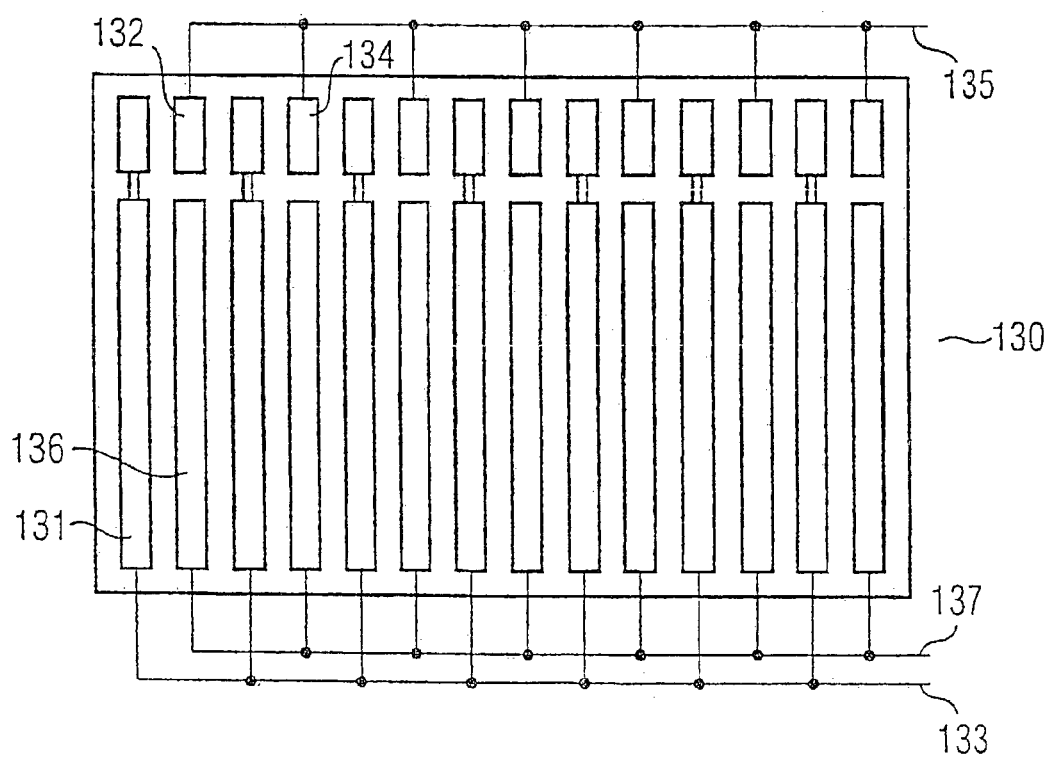

FIG. 1c shows a third exemplary embodiment of a biosensor 130, in which the first overall electrode 131 is formed by a multiplicity of first part-electrodes which are connected in parallel and intermesh with a multiplicity of electrode segments which, connected in parallel, form the second overall electrode 132.

The first part-electrodes 131 are each coupled to a first electrical connection 133. The first electrode segments 134 of the second overall electrode 132 are connected in parallel and are electrically coupled to a second electrical connection 135.

The second electrode segments 136 of the second overall electrode 132 are connected in parallel and are each electrically coupled to a third electrical connection 137.

The interdigitated electrode arrangement basically corresponds to the electrode arrangement which is known from [4], except that the second electrode is now divided into two, or in general terms any desired number n of electrode segments which are electrically insulated from one another, are connected in parallel and can each be selected and therefore electrically coupled independently of one another.

Figure 6A:
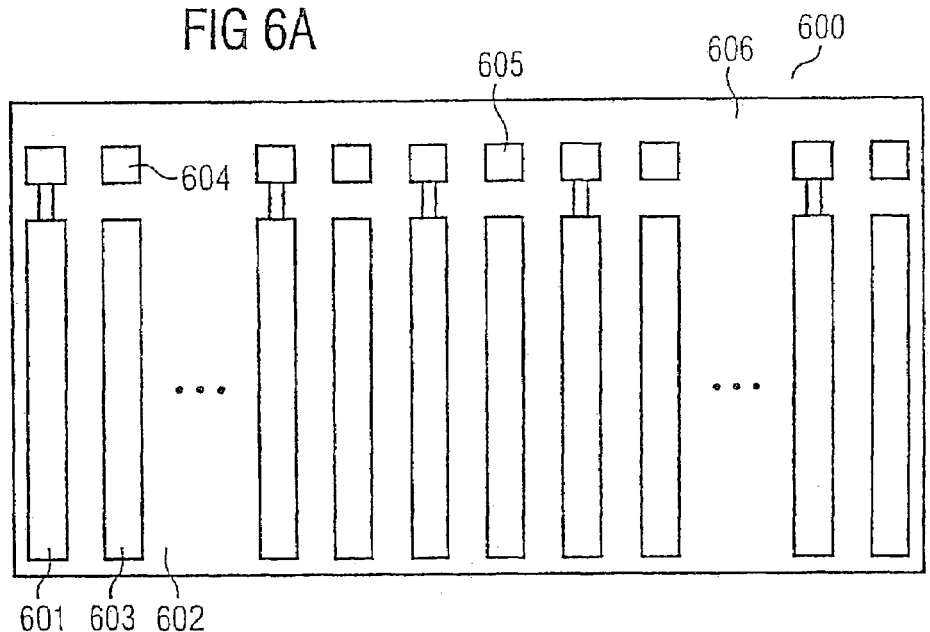
FIGS. 6a and 6b show a sketch of a further electrode arrangement in accordance with a further exemplary embodiment of the invention.

FIG. 6a shows an example of an electrode arrangement having a number of three electrode segments of the second electrode.

The biosensor 600 in accordance with this exemplary embodiment therefore has a multiplicity of first electrodes 601 and a multiplicity of second electrodes 602.

The second electrodes 602 have a multiplicity of first electrode segments 603, a multiplicity of second electrode segments 604 and a multiplicity of third electrode segments 605, the individual electrode segments 603, 604, 605 being electrically insulated from one another by means of an insulator layer 606.

Figure 6B:
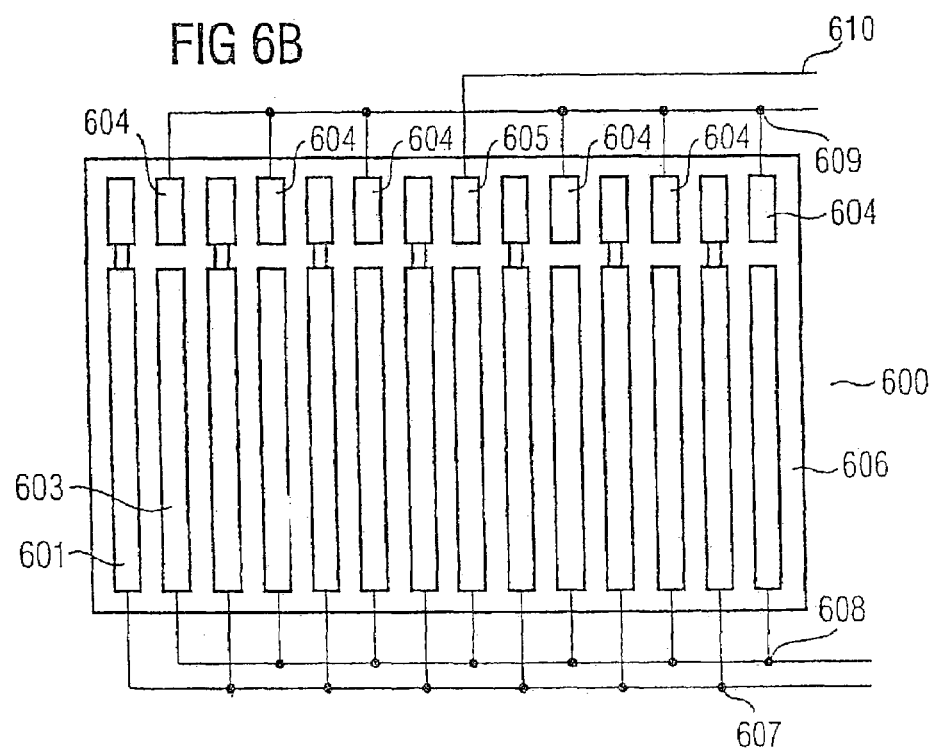

As illustrated in FIG. 6b, the first electrodes 601 are each coupled to a first electrical connection 607 and thereby connected in parallel.

Furthermore, the first electrode segments 603 of the second electrode 602 are connected in parallel and are each coupled to a second electrical connection 608.

Furthermore, the second electrode segments 604 of the second electrode 602 are connected in parallel and electrically coupled to a third electrical connection 609.

Furthermore, the third electrode segments 605 are likewise connected in parallel and electrically coupled to a fourth electrical connection 610.

By suitably selecting the electrode segments 603, 604, 605 and the way in which they are electrically connected, as explained in more detail below, it is possible to vary and adjust the size of the effective electrode face very accurately, so that the measurement current can be kept within a very accurately defined dynamic range.

Figure 7:
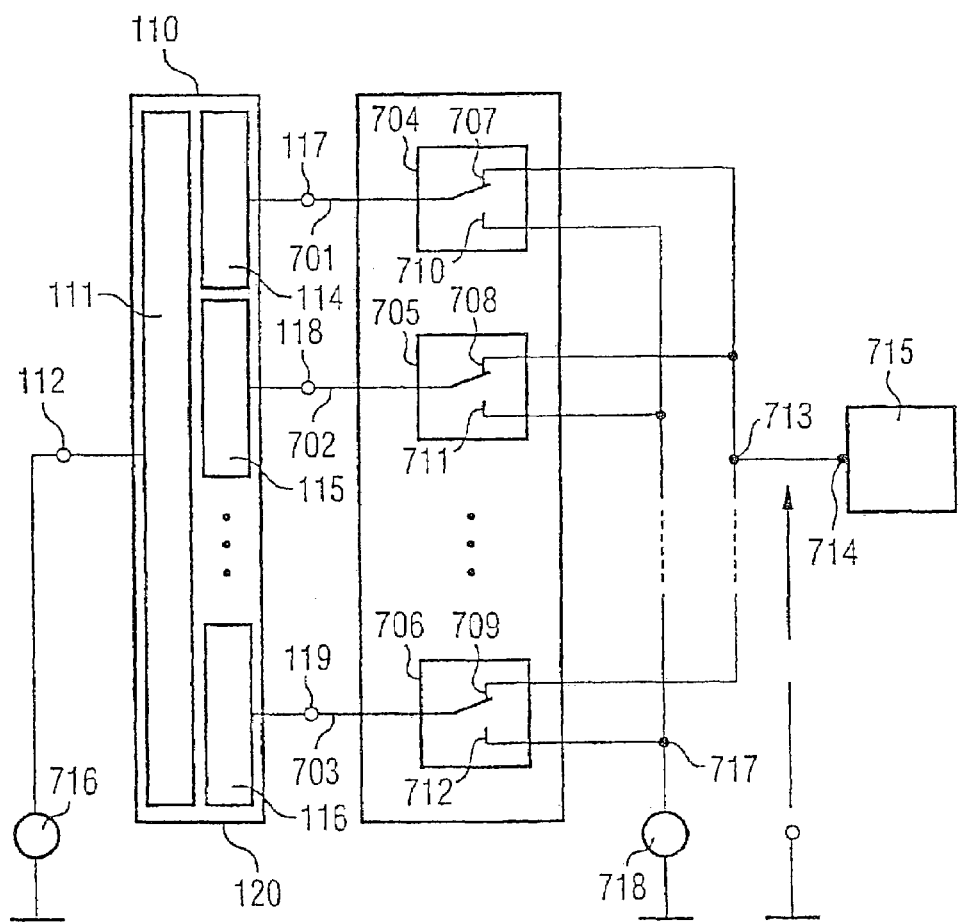
FIG. 7 shows a biosensor with switches and measurement electronics coupled to the switches in accordance with an exemplary embodiment of the invention.

FIG. 7 shows a circuit of the biosensor 110 illustrated in FIG. 1b.

The electrical connections 117, 118, 119 of the electrode segments 114, 115, 116 of the second electrode 113 are electrically coupled to electrical switches 704, 705, 706 via electrical links 701, 702, 703, in each case one of the electrical switches 704, 705, 706 being electrically coupled to an electrical connection 117, 118, 119.

In a first switch position, each electrical switch 704, 705, 706 is electrically coupled to a first switch connection 707, 708, 709, and in a second switch position each electrical switch 704, 705, 706 is electrically coupled to a second switch connection 710, 711, 712.

The first switch connections 707, 708, 709 are electrically coupled to one another by means of a first common connection 713, and furthermore the first common connection 713 is electrically coupled to the input 714 of measurement electronics 715.

Furthermore, FIG. 7 shows a first voltage source 716, which is electrically coupled to the first electrical connection 112 of the first electrode 111, so that the first electrical potential V1 is applied to the first electrode 111.

The second switch connections 710, 711, 712 are electrically coupled to one another by means of a second common connection 717, which is electrically coupled to a second voltage source 718, with the result that the second electrical potential V2 is applied to the electrode segments which are each coupled to the second switch connection 710, 711, 712 by means of the switches 704, 705, 706.

The electrical coupling of the second voltage source 718 to the second switch connections 710, 711, 712 ensures that the reduction/oxidation recycling operation remains unaffected by the respective switch position of the switches 704, 705, 706. The circuit arrangement illustrated also ensures that the circuit is operated at a constant working point independently of the switch position of the individual switches 704, 705, 706.

Furthermore, the second electrical potential V2 is also applied to the first common connection 713 and therefore also to the selected electrode segments which are coupled to the input 714 of the measurement electronics 715 by means of the switches 704, 705, 706 via the first switch connections 707, 708, 709.

In accordance with this exemplary embodiment, as illustrated in FIG. 7, the first electrode segment 114 and the second electrode segment 115 of the second electrode 113 are electrically connected to the first switch connection 707, 708 by means of the first switch 704 and the second switch 705 and are thereby coupled to the measurement electronics 715.

This means that the current which is generated at the first electrode segment 114 and the second electrode segment 115 is tapped from the second electrode 113 and fed to the measurement electronics 715 via the switches 704, 705.

Figure 8A:
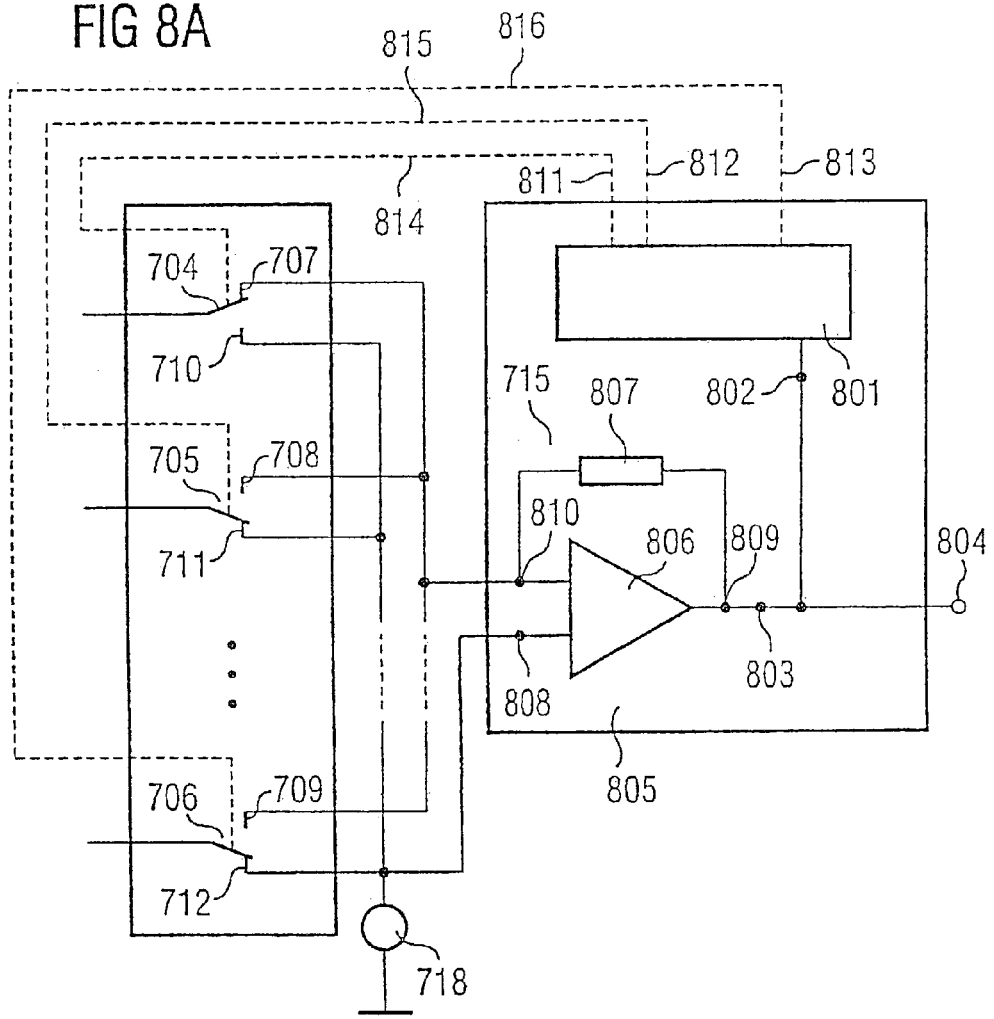
FIGS. 8a and 8b show a sketch of a biosensor with measurement electronics and a switch selection unit coupled to the measurement electronics in accordance with an exemplary embodiment of the invention (FIG. 8a) and of a selection element of the switch selection unit (FIG. 8b).

As illustrated in FIG. 8a, a switch selection unit 801 can be coupled to the measurement electronics 715 via its input 802, in such a manner that the output 803 of the measurement electronics is coupled both to an external connection 804, at which an output voltage $V_{out}$ can be tapped, and to the input 802 of the switch selection unit 801.

The measurement electronics 715 has a current-voltage converter 805 which has an operational amplifier 806 and an electrical resistor 807.

The noninverting input 808 of the operational amplifier 806 is electrically coupled to the second voltage source 718.

Furthermore, the output 809 of the operational amplifier 806 is electrically coupled, via the electrical resistor 807, to the inverting input 810 of the operational amplifier 806 and to the first common connection 713.

The switch selection unit 801 is designed in such a manner that various ranges of values are predetermined by means of comparators, and, depending on the output voltage $V_{out}$, the switches 704, 705, 706 to which outputs 811, 812, 813 of the switch selection unit 801 are coupled in such a manner that the switches 704, 705, 706 can be controlled by means of a respective output signal, represented in FIG. 8 by means of dashed lines 814, 815, 816, so that the respective switch 704, 705, 706 can be switched either into the first switch position or into the second switch position and remains in this switch position until a changed control signal is applied to the corresponding output 811, 812, 813 of the switch selection unit 801 on account of the output signal, i.e. the control signal.

The switch selection unit 801 has, by way of example, n selection elements 817, the number n of which corresponds to the number of electrode segments which can be selected.

Figure 8B:
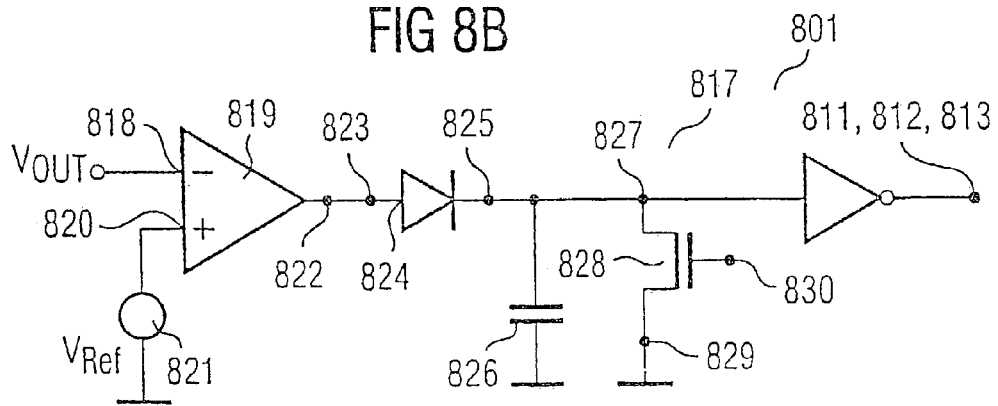

Each selection element 817 has in each case the configuration illustrated in FIG. 8b.

The output voltage $V_{out}$ is present at the inverting input 818 of an operational amplifier 819 of the respective selection element 817. A reference comparator voltage Vref, which is predetermined specifically for each selection element 817 and is symbolized in FIG. 8b by a voltage source 821, is applied to the noninverting input 820 of the operational amplifier 819.

The output 822 of the operational amplifier 819 is coupled to an input 823 of a diode 824. The output 825 of the diode 824 is coupled to a capacitor 826, which is coupled to ground potential by means of its other connection.

Furthermore, the output 825 of the diode 824 is coupled to the drain connection 827 of an initializing transistor 828. The source connection 829 of the initializing transistor 828 is coupled to ground potential. The selection element 817 is initialized by means of the gate connection 830 of the initializing transistor 828 with the aid of an initializing signal.

Furthermore, the output 825 of the diode 824 is coupled to an input 831 of an inverter 832. The output 833 of the inverter 832 is coupled to the respective output 811, 812, 813 of the switch selection unit 801.

On account of the selection element 817, the corresponding switch, on account of the output voltage $V_{out}$ rising above the value of the respectively predetermined reference comparator voltage $V_{ref}$, which is coupled to the respective selection element 817, is switched and moved into the second switch position, so that the corresponding electrode segment makes no further contribution to the current flowing into the measurement electronics 715.

Any desired, free selection of the electrode segments of the second electrode is achieved very easily and flexibly in this way.

In an alternative embodiment, it is provided for the first electrode to be divided into electrode segments and for the corresponding measurement electronics in accordance with the exemplary embodiment described above and the switch selection unit to be capable of being electrically coupled to the electrode segments of the first electrode.

It should be noted that the invention is not restricted to a reduction/oxidation operation, but rather the arrangement according to the invention can be used in any area in which the requirements of a considerably varying dynamic range of a measurement signal are to be compensated for.

Furthermore, it should be noted that the invention is not restricted to the planar electrodes which are known from the prior art.

For example, in an alternative embodiment it is possible to provide a third electrode, which is preferably arranged between the first electrode and the second electrode and/or the electrode segments thereof, so that the reduction/oxidation process takes place as part of the reduction/oxidation operation between the third electrode and the second electrode.

This can be ensured in particular by applying a third electrical potential, which is greater than the second electrical potential V2 and than the first electrical potential V1, to the third electrode. Furthermore, a second electrical potential V2, which is lower than the first electrical potential V1 which is applied to the first electrode is applied to the second electrode.

Furthermore, as part of an alternative embodiment, electrodes which are arranged in such a manner relative to one another that substantially uncurved field lines of an electric field generated between the electrodes can form between the electrodes.

This can be achieved, by way of example, by means of electrode arrangements as explained in more detail below with reference to FIGS. 9 to 19A to G.

FIG. 9 shows a biosensor chip 900 with a further electrode configuration.

The biosensor chip 900 has a first electrode 901 and a second electrode 902, which are arranged on an insulator layer 903 in such a way that the first electrode 901 and the second electrode 902 are electrically insulated from one another.

The first electrode 901 is coupled to a first electrical terminal 904, and the second electrode 902 is coupled to a second electrical terminal 905.

The electrodes 901, 902 have a cuboid structure, with a first electrode face 906 of the first electrode 901 and a first electrode face 907 of the second electrode 902 facing one another while being aligned essentially parallel.

This is achieved, according to this exemplary embodiment, by the fact that the electrodes 901, 902 have side walls 906, 907 which are essentially perpendicular with respect to the surface 508 of the insulator layer 903, and which respectively form the first electrode face 906 of the first electrode 901 and the first electrode face 907 of the second electrode 902.

If an electric field is applied between the first electrode 901 and the second electrode 902, then owing to the electrode faces 906, 907 which are aligned essentially parallel with one another, a field line profile is produced with field lines 909 which are essentially uncurved between the faces 906, 907.

Curved field lines 910 occur only between a second electrode face 911 of the first electrode 901 and a second electrode face 912 of the second electrode 902, which respectively form the upper surface for the electrodes 901, 902, as well as in an edge region 913 between the electrodes 901, 902.

The first electrode faces 906, 907 of the electrodes 901, 902 are formed as holding regions for holding probe molecules, which can bind macromolecular biopolymers that are detected by means of the biosensor 900.

The electrodes 901, 902 are made of gold according to this exemplary embodiment.

Covalent bonds are produced between the electrodes and the probe molecules, the sulfur for forming a gold-sulfur coupling being present in the form of a sulfide or a thiol.

For the case in which DNA probe molecules are used as the probe molecules, such sulfur functionalities are part of a modified nucleotide which is incorporated by means of phosphoramidite chemistry during an automated DNA synthesis method at the 3' end or at the 5' end of the DNA strand to be immobilized. The DNA probe molecule is therefore immobilized at its 3' end or at its 5' end.

For the case in which ligands are used as the probe molecules, the sulfur functionalities are formed by one end of an alkyl linker or of an alkylene linker, the other end of which has a chemical functionality suitable for the covalent bonding of the ligand, for example a hydroxyl radical, an acetoxy radical or a succinimidyl ester radical.

The electrodes, i.e. in particular the holding regions, are covered during measurement use with an electrolyte 914, in general with a solution to be analyzed.

If the solution 914 to be analyzed contains the macromolecular biopolymers to be recorded, for example DNA strands to be recorded which have a predetermined sequence and which can hybridize with the immobilized DNA probe molecules on the electrodes, then the DNA strands hybridize with the DNA probe molecules.

If the solution 914 to be analyzed does not contain any DNA strands with the sequence complementary to the sequence of the DNA probe molecules, then no DNA strands from the solution 914 to be analyzed can hybridize with the DNA probe molecules on the electrodes 901, 902.

As has been explained above, a redox recycling operation is started between the electrodes 901, 902, and in this way the number of marked hybridized DNA strands, generally of the marked, bound macromolecular biopolymers is determined.

Figure 10:
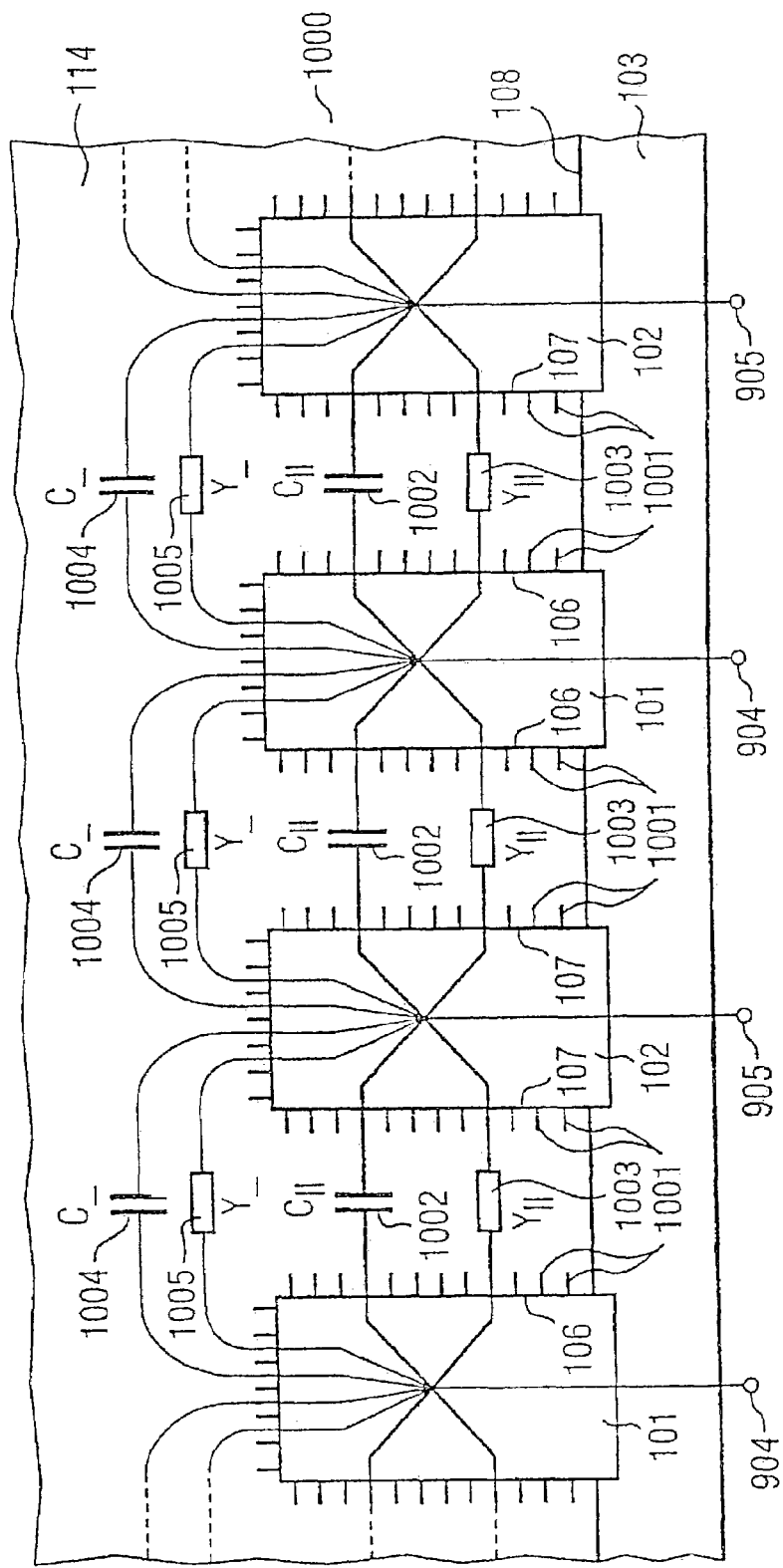
FIG. 10 shows a cross section through a biosensor with two electrodes which are arranged as an interdigitated electrode arrangement.

FIG. 10 shows a biosensor 1000 with a further electrode configuration according to a further exemplary embodiment of the invention.

In the biosensor 1000, in the same way as in the biosensor 900 according to the exemplary embodiment shown in FIG. 9, two electrodes 901, 902 are provided which are applied on the insulator layer 903.

In contrast to the biosensor 900 with only two cuboid electrodes, the two electrodes according to the biosensor 1000 represented in FIG. 10 are arranged as a plurality of respectively alternately arranged, parallel-connected electrodes in the form of the known interdigitated electrode arrangement.

For further illustration, FIG. 10 also shows a schematic electrical equivalent circuit diagram, which is indicated in the representation of the biosensor 1000.

Since essentially uncurved field lines occur with respect to the surface 908 of the insulator layer 903 between the electrode faces 906, 907 of the electrodes 901, 902, which face one another while being essentially parallel, as was represented in FIG. 9, the component of the first capacitance 1002 and of the first admittance 1003 produced by the uncurved field lines predominates compared with the second capacitance 1004 and the second admittance 1005, which are produced by the curved field lines 910.

This significantly greater component of the first capacitance 1002 and of the first admittance 1003 in relation to the total admittance, which is obtained from the sum of the first capacitance 1002 and the second capacitance 1004 as well as the first admittance 1003 and the second admittance 1005, has the effect of significantly increasing the sensitivity of the biosensor 1000 when the state of the biosensor 1000 changes, i.e. when DNA strands in the solution 914 to be analyzed hybridize with DNA probe molecules 1001 immobilized on the holding regions on the electrode faces 906, 907.

Clearly, with the same lateral dimensions of the electrodes 901, 902 and the same dimensions of the previously introduced active region, i.e. with the same area of the holding regions on the electrode faces, a substantially greater component of field lines of an applied electric field between the electrodes 901, 902 is therefore contained in the volume in which the hybridization takes place when DNA strands to be recorded are contained in the solution 914 to be analyzed, than in the case of a planar electrode arrangement.

In other words, this means that the capacitance of the arrangement according to the invention per unit chip area is significantly greater than the capacitance per unit chip area in the case of a planar electrode arrangement.

A few alternative possibilities for producing a cuboid sensor electrode with essentially vertical side walls will be explained below.

Figure 11A:
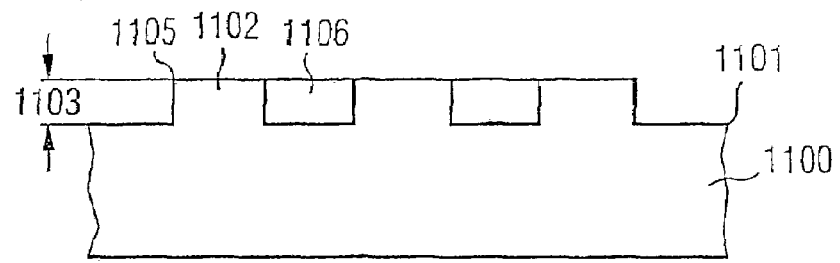
FIGS. 11a to 11d show cross-sectional views through an interdigitated electrode in four method states in a method for producing a biosensor in accordance with an exemplary embodiment of the invention.
Figure 11B:
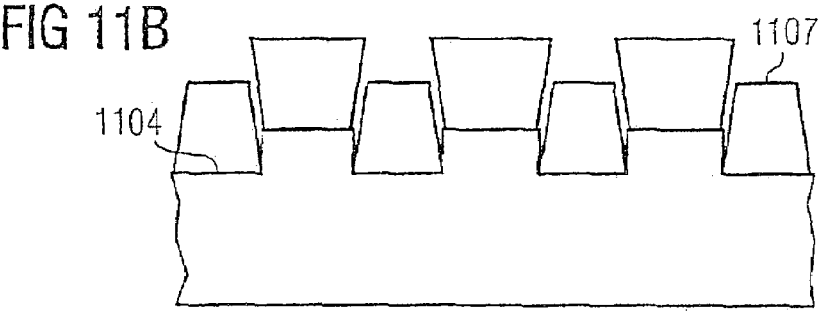
Figure 11C:
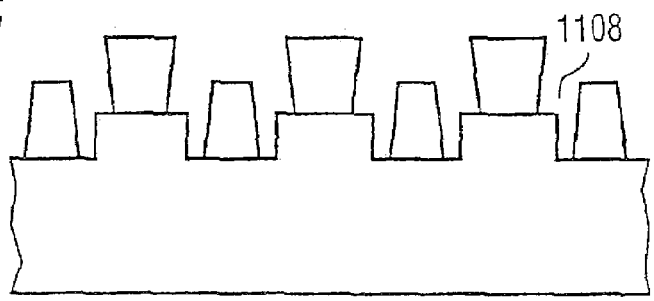
Figure 11D:
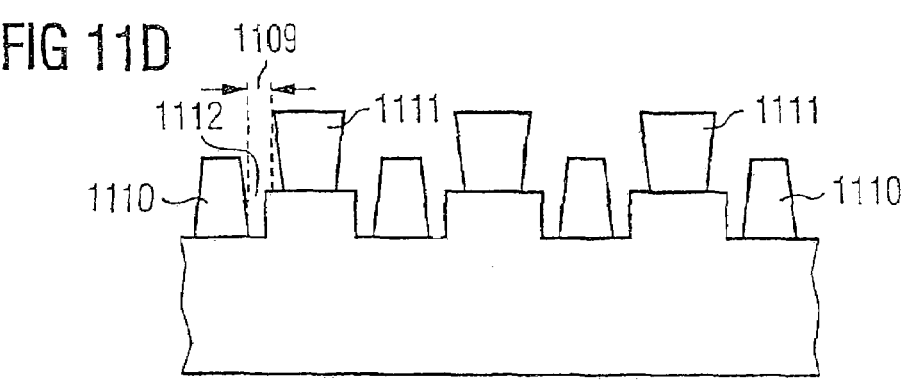

First Method for Producing Metal Electrodes with Essentially Vertical Side Walls, which can Immobilize Probe Molecules FIG. 11a shows a silicon substrate 1100, as is produced for known CMOS processes.

On the silicon substrate 1100, which already contains integrated circuits and/or electrical terminals for the electrodes to be formed, an insulator layer 1101 which is also used as a passivation layer is applied with a sufficient thickness, with a thickness of 500 nm according to the exemplary embodiment, by means of a CVD method.

The insulator layer 1101 may be made of silicon oxide $SiO_2$ or silicon nitride $Si_3N_4$.

The interdigitated arrangement of the biosensor 1000 according to the exemplary embodiment described above is defined by means of photolithography on the insulator layer 1101.

By means of a dry etching method, e.g. reactive ion etching (RIE), steps 1102 are subsequently produced, i.e. etched, in the insulator layer 1101 with a minimum height 1103 of approximately 100 nm according to the exemplary embodiment.

The height 1103 of the steps 1102 must be large enough for a subsequent self-aligning process to form the metal electrode.

It should be pointed out that an evaporation coating method or a sputtering method may alternatively also be used for applying the insulator layer 1101.

During the structuring of the steps 1102, care should be taken that the flanks of the steps 1102 are steep enough so that they form sufficiently sharp edges 1105. An angle 1106 of the step flanks, measured with respect to the surface of the insulator layer 1101, should be at least 50 degrees according to the exemplary embodiment.

In a further step, an auxiliary layer 1104 (cf. FIG. 11b) made of titanium with a thickness of approximately 10 nm is applied to the stepped insulator layer 1101.

The auxiliary layer 1104 may comprise tungsten and/or nickel-chromium and/or molybdenum.

It is necessary to guarantee that the metal layer applied in a further step, according to the exemplary embodiment a metal layer 1107 made of gold, grows porously at the edges 1105 of the steps 1102 so that, in a further method stage, it is possible to respectively etch a gap 1108 at the step junctions, into the gold layer 1107 which is applied surface-wide.

The gold layer 1107 for the biosensor 1000 is applied in a further method step.

According to the exemplary embodiment, the gold layer has a thickness of from approximately 500 nm to approximately 2000 nm.

In terms of the thickness of the gold layer 1107, it is merely necessary to guarantee that the thickness of the gold layer 1107 is sufficient for the gold layer 1107 to grow porously in columns.

In a further step, openings 1108 are etched into the gold layer 1107 so that gaps are formed.

For wet etching of the openings, an etchant solution made up of 7.5 g of Super Strip 100™ (trademark of Lea Ronal GmbH, Germany) and 20 g KCN in 1000 ml of water $H_2O$ is used.

Owing to the columnar growth of the gold, in general of the metal, during the evaporation coating onto the adhesion layer 1104, anisotropic etching attack is achieved so that the surface erosion of the gold takes place approximately in the ratio 1:3.

The gaps 1108 are formed as a function of the duration of the etching process by the etching of the gold layer 1107.

This means that the duration of the etching process dictates the basic width, i.e. the distance 1109 between the gold electrodes 1110, 1111 which are being formed.

After the metal electrodes have a sufficient width and the distance 1109 between the gold electrodes 1110, 1111 which are being formed is achieved, the wet etching is ended.

It should be noted that, because of the porous evaporation coating, etching in a direction parallel to the surface of the insulator layer 1101 takes place substantially faster than in a direction perpendicular to the surface of the insulator layer 1101.

It should be pointed out that alternatively to a gold layer, it is possible to use other noble metals, for example platinum, titanium or silver, since these materials can likewise have holding regions or can be coated with a suitable material for holding immobilized DNA probe molecules, or in general for holding probe molecules, and they exhibit columnar growth during evaporation coating.

For the case in which the adhesion layer 1104 needs to be removed in the opened columns 1112 between the metal electrodes 1110, 1111, this is likewise carried out in a self-aligning fashion by using the gold electrodes 1110, 1111 as an etching mask.

Compared with the known interdigitated electrodes, the structure according to this exemplary embodiment has the advantage, in particular, that owing to the self-aligning opening of the gold layer 1107 over the edges 1105, the distance between the electrodes 1110, 1111 is not tied to a minimum resolution of the production process, i.e. the distance 1109 between the electrodes 1110, 1111 can be kept very narrow.

According to this method, the biosensor 1000 according to the exemplary embodiment represented in FIG. 10 with the corresponding metal electrodes is therefore obtained.

Figure 12A:
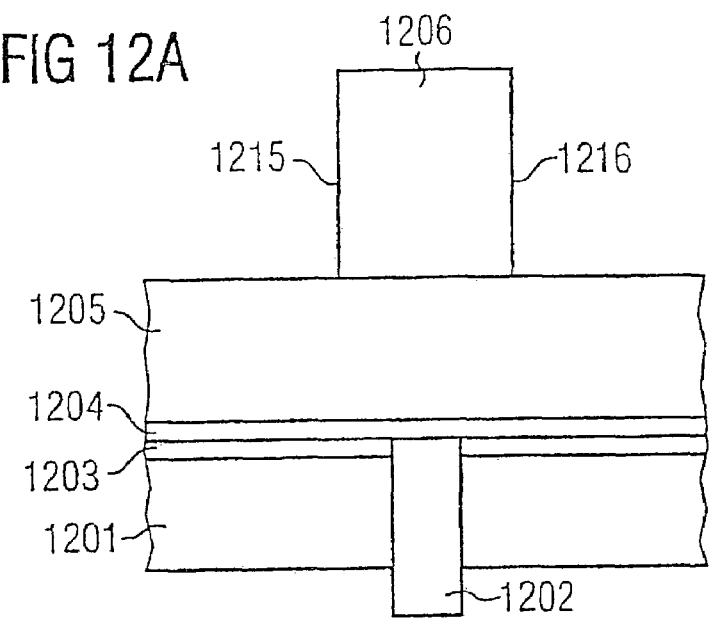
FIGS. 12a to 12c show cross-sectional views through a biosensor during individual method steps of the method for producing an electrode of the biosensor in accordance with a further exemplary embodiment of the invention.
Figure 12B:
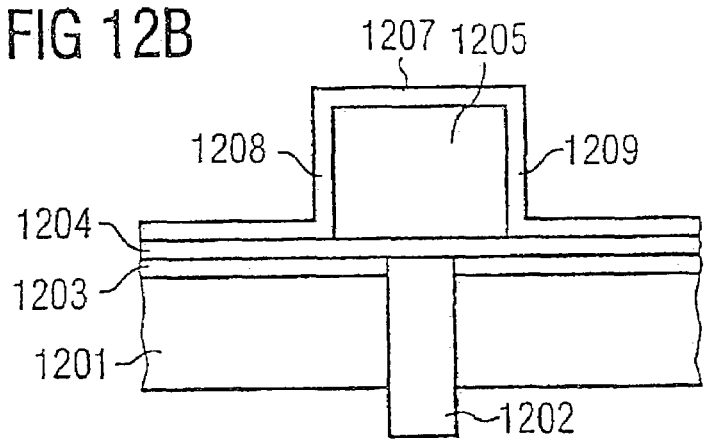
Figure 12C:
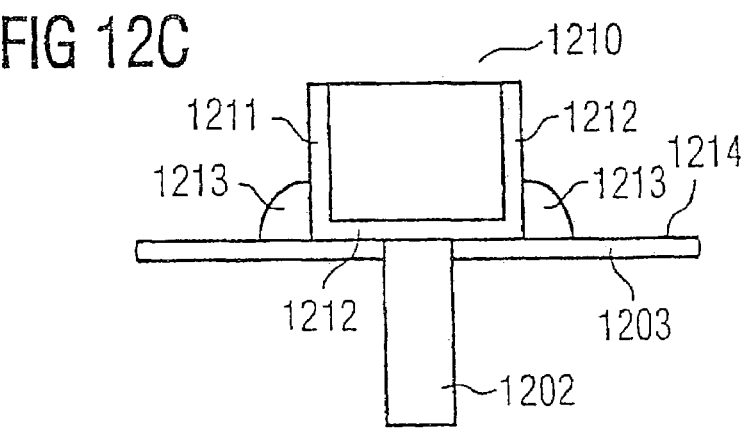

Second Method for Producing Metal Electrodes with Essentially Vertical Side Walls, which can Immobilize Probe Molecules The production method represented in FIG. 12a to FIG. 12c starts with a substrate 1201, for example a silicon substrate wafer (cf. FIG. 12a), on which metallization 1202 is already provided as an electrical terminal, an etch stop layer 1203 of silicon nitride $Si_3N_4$ already having been applied on the substrate 1201.

A metal layer 1204, according to the exemplary embodiment a gold layer 1204, is applied on the substrate by means of an evaporation coating method.

Alternatively, a sputtering method or a CVD method may also be used to apply the gold layer 1204 to the etch stop layer 1203.

In general, the metal layer 1204 comprises the metal from which the electrode to be formed is intended to be formed.

An electrically insulating auxiliary layer 1205 of silicon oxide $SiO_2$ is applied on the gold layer 1204 by means of a CVD method (alternatively by means of an evaporation coating method or a sputtering method).

By using photolithographic technology, a resist structure, for example a cuboid structure, is formed from a resist layer 1206, which corresponds to the shape of the electrode to be formed.

If a biosensor array, described below, with a plurality of electrodes is to be produced, a resist structure whose shape corresponds to the electrodes to be formed, which form the biosensor array, is produced by means of photolithography.

Put another way, this means that the lateral dimensions of the resist structure which is formed correspond to the dimensions of the sensor electrode to be produced.

After application of the resist layer 1206 and the corresponding illumination, which defines the corresponding resist structures, the resist structure is removed in the "undeveloped", i.e. unilluminated regions, for example by means of ashing or wet chemically.

The auxiliary layer 1205 is also removed by means of a wet etching method or a dry etching method in the regions not protected by the photoresist layer 1206.

In a further step, after removal of the resist layer 1206, a further metal layer 1207 is applied conformally as an electrode layer over the remaining auxiliary layer 1205, in such a way that the side faces 1208, 1209 of the residual auxiliary layer 1205 are covered with the electrode material, according to the exemplary embodiment with gold (cf. FIG. 12b).

The application may be carried out by means of a CVD method or a sputtering method or by using an ion metal plasma method.

In a last step (cf. FIG. 12c), spacer etching is carried out, during which the desired structure of the electrode 1210 is formed by deliberate over-etching of the metal layers 1204, 1207.

The electrode 1210 therefore has the spacers 1211, 1212, which have not been etched away in the etching stage of etching the metal layers 1204, 1207, as well as the part of the first metal layer 1204, arranged immediately below the residual auxiliary layer 1205, which has not been etched away by means of the etching method.

The electrode 1210 is electrically coupled to the electrical terminal, i.e. the metallization 1202.

The auxiliary layer 1205 of silicon oxide may if necessary be removed by further etching, for example in the plasma or wet chemically, by means of a method in which selectivity with respect to the etch stop layer 1203 is provided.

This is guaranteed, for example, if the auxiliary layer 1205 consists of silicon oxide and the etch stop layer 1203 comprises silicon nitride.

The steepness of the walls of the electrode in the biosensor chip 900, 1000, represented by the angle 1213 between the spacers 1211, 1212 and the surface 1214 of the etch stop layer 1203, is therefore determined by the steepness of the flanks of the residual auxiliary layer 1205, i.e. in particular the steepness of the resist flanks 1215, 1216 of the structured resist layer 1206.

Third Method for Producing Metal Electrodes with Essentially Vertical Side Walls, which can Immobilize Probe Molecules FIG. 13a to FIG. 13c represent a further possibility for producing an electrode within essentially vertical walls.

This also, as represented in the second example of producing an electrode, starts with a substrate 1301 on which a metallization 1302 is already provided for the electrical terminal of the biosensor electrode to be formed.

A metal layer 1303 is evaporation coated as an electrode layer on the silicon substrate 1301, the metal layer 1303 comprising the material to be used for the electrode, according to this exemplary embodiment gold.

Alternatively to evaporation coating of the metal layer 1303, the metal layer 1303 may also be applied on the substrate 1301 by means of a sputtering method or by means of a CVD method.

A photoresist layer 1304 is applied on the metal layer 1303 and is structured by means of photolithographic technology so as to produce a resist structure which, after development and removal of the developed regions, corresponds to the lateral dimensions of the electrode to be formed, or in general of the biosensor array to be formed.

The thickness of the photoresist layer 1304 corresponds essentially to the height of the electrodes to be produced.

During structuring in a plasma with process gases which cannot lead to any reaction of the electrode material, in particular in an inert gas plasma, for example with argon as the process gas, the erosion of the material according to this exemplary embodiment is carried out by means of physical sputter erosion.

In this case, the electrode material is sputtered from the metal layer 1303 in a redeposition process onto the essentially vertical side walls 1305, 1306 of the structured resist elements that are not removed after ashing the developed resist structure, where it is no longer exposed to any sputter attack.

Redeposition of electrode material onto the resist structure protects the resist structure from further erosion.

Because of the sputtering, side layers 1307, 1308 of the electrode material, according to the exemplary embodiment of gold, are formed at the side walls 1305, 1306 of the resist structure.

The side layers 1307, 1308 are electrically coupled to an unremoved part 1309 of the metal layer 1303, which lies immediately below the residual resist structure 1306, and furthermore to the metallization 1303 (cf. FIG. 13b).

In a last step (cf. FIG. 13c), the resist structure 1306, i.e. the photoresist which is found in the volume formed by the side walls 1307, 1308 as well as the remaining metal layer 1309, is removed by means of ashing or wet chemically.

The result is the electrode structure 1310 represented in FIG. 13c, which is formed with the side walls 1307, 1308 as well as the unremoved part 1309, which forms the bottom of the electrode structure and is electrically coupled to the metallization 1303.

As in the production method presented above, the steepness of the side walls 1307, 1308 of the electrode that is formed in this method is determined by the steepness of the resist flanks 1305, 1306.

FIG. 14a to FIG. 14c represent a further exemplary embodiment of the invention with cylindrical electrodes protruding perpendicularly from the substrate.

In order to produce the biosensor 1400 with cylindrical electrodes, which are arranged essentially perpendicularly on a substrate 1401 of silicon oxide, a metal layer 1402 is applied by means of an evaporation coating method as an electrode layer of the desired electrode material, according to the exemplary embodiment of gold.

A photoresist layer is applied on the metal layer 1402, and the photoresist layer is illuminated by means of a mask so that the cylindrical structure 1403 represented in FIG. 14a is obtained on the metal layer 1402 after the unilluminated regions have been removed.

The cylindrical structure 1403 has a photoresist torus 1404 as well as a cylindrical photoresist ring 1405, which is arranged concentrically around the photoresist torus 1404.

The photoresist is removed between the photoresist torus 1404 and the photoresist ring 1405, for example by means of ashing or wet chemically.

Through the use of a sputtering method, as in conjunction with the method described above for producing an electrode, a metal layer 1406 is applied around the photoresist torus 1404 by means of a redeposition process.

In a similar way, an inner metal layer 1407 is formed around the photoresist ring 1405 (cf. FIG. 14b).

In a further step, the structured photoresist material is removed by means of ashing or wet chemically, so that two cylindrical electrodes 1408, 1409 are formed.

The substrate 1401 is removed in a last stage, for example by means of a plasma etching process that is selective with respect to the electrode material, to the extent that the metallizations in the substrate are exposed and electrically couple to the cylindrical electrodes.

The inner cylindrical electrode 1408 is therefore electrically coupled to a first electrical terminal 1410, and the outer cylindrical electrode 1409 is electrically coupled to a second electrical terminal 1411.

The residual metal layer 1402, which has not yet been removed by the sputtering between the cylindrical electrodes 1408, 1409, is removed in a last step by means of a sputter-etching process. The metal layer 1402 is likewise removed in this way.

It should be mentioned in this context that, according to this exemplary embodiment as well, the metallizations for the electrical terminals 1410, 1411 are already provided in the substrate 1401 at the start of the method.

FIG. 15 shows a plan view of a biosensor array 1500, in which cylindrical electrodes 1501, 1502 are contained.

Each first electrode 1501 has a positive electrical potential.

Each second electrode 1502 of the biosensor array 1500 has an electrical potential that is negative in relation to the respectively neighboring first electrode 1501.

The electrodes 1501, 1502 are arranged in rows 1503 and columns 1504.

The first electrode 1501 and the second electrode 1502 are respectively arranged alternately in each row 1503 and each column 1504, i.e. a second electrode 1502 is respectively arranged in a row 1503 or a column 1504 immediately next to a first electrode 1501, and a first electrode 1501 is respectively arranged in a row 1503 or a column 1504 next to a second electrode 1502.

This ensures that an electric field with essentially uncurved field lines in the height direction of the cylinder electrodes 1501, 1502 can be produced between the individual electrodes.

As described above, a large number of DNA probe molecules are respectively immobilized on the electrodes.

If a solution to be analyzed (not shown) is then applied to the biosensor array 1500, then the DNA strands hybridize with DNA probe molecules complementary thereto which are immobilized on the electrodes.

In this way, by means of the redox recycling operation described above, the existence or nonexistence of DNA strands of a predetermined sequence in a solution to be analyzed can in turn be detected by means of the biosensor array 1500.

FIG. 16 shows a further exemplary embodiment of a biosensor array 1600 with a plurality of cuboid electrodes 1601, 1602.

The arrangement of the cuboid electrodes 1601, 1602 is in accordance with the arrangement of the cylindrical electrodes 1501, 1502 as presented in FIG. 15 and explained above.

Figure 17:
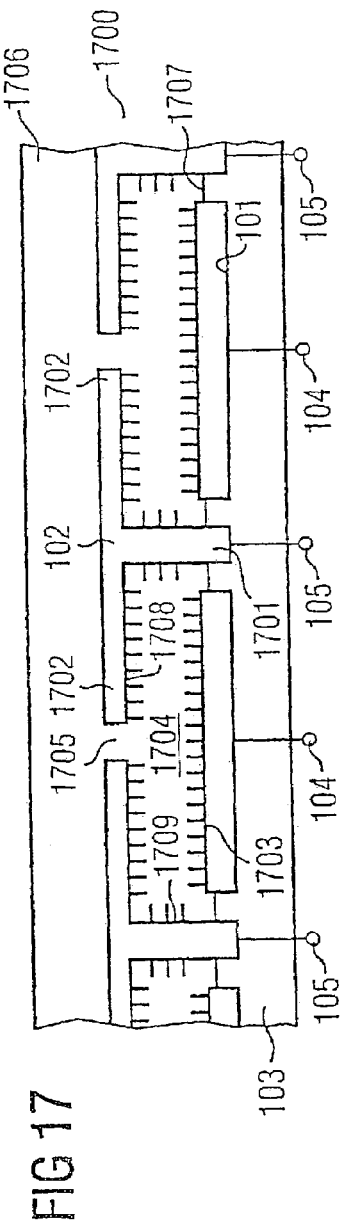
FIG. 17 shows a cross-sectional view of a biosensor in accordance with a further exemplary embodiment of the invention.

FIG. 17 shows an electrode arrangement of a biosensor chip 1700 according to a further exemplary embodiment of the invention.

The first electrode 901 is applied on the insulator layer 903 and is electrically coupled to the first electrical terminal 904.

The second electrode 902 is likewise applied on the insulator layer 903 and is electrically coupled to the second electrical terminal 905.

As shown in FIG. 17, the second electrode according to this exemplary embodiment has a different shape compared with the second electrode described previously.

The first electrode, as can be seen from FIG. 17, is a planar electrode and the second electrode is configured with a T-shape.

Each T-shaped second electrode has a first branch 1701, which is arranged essentially perpendicular to the surface 1707 of the insulator layer 903.

Furthermore, the second electrode 902 has second branches 1702 which are arranged perpendicular to the first branch 1701 and are arranged at least partially over the surface 1703 of the respective first electrode 901.

As can be seen in FIG. 17, several first electrodes 901 and several second electrodes 902 are connected in parallel, so that because of the T-shaped structure of the second electrode 902, a cavity 1704 is created which is formed by two second electrodes 902 arranged next to one another, one first electrode 901 and the insulator layer 903.

The individual first and second electrodes 901, 902 are electrically insulated from one another by means of the insulator layer 903.

An opening 1705 is provided between the individual second branches 1702 of the second electrode 902 for each cavity 1704, which opening 1705 is large enough so that when an electrolyte 1706 is being applied to the biosensor 1700, the electrolyte and DNA strands possibly contained in the solution 1706 to be analyzed, for example an electrolyte, can pass through the opening 1705 into the cavity 1704.

DNA probe molecules 1709, which can hybridize with the corresponding DNA strands of a predetermined sequence that are to be recorded, are immobilized on holding regions on the first and second electrodes.

As can be seen in FIG. 17, because of the mutually facing surfaces, aligned essentially parallel with one another, of the second electrode 1708 and of the first electrode 1703, on which the holding regions for holding the DNA probe molecules 1709 are provided, essentially uncurved field lines are formed when an electric field is applied between the first electrode 901 and the second electrode 902.

Figure 18:
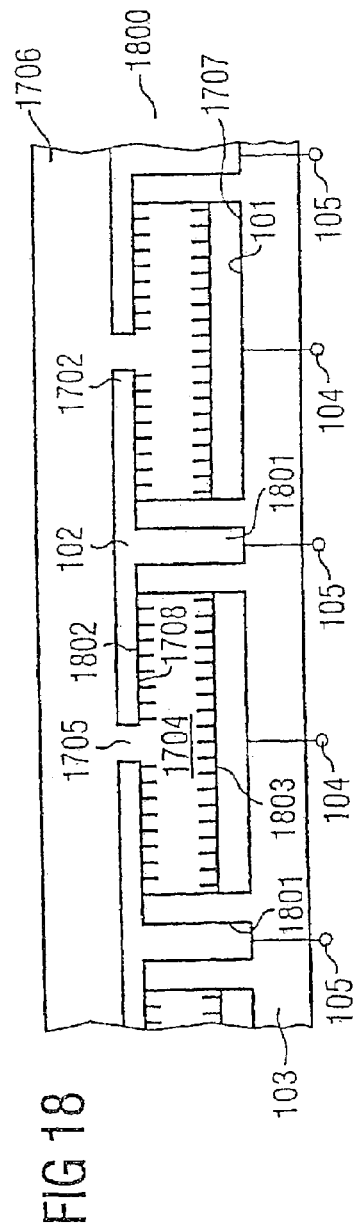
FIG. 18 shows a cross-sectional view of a biosensor in accordance with a further exemplary embodiment of the invention.

FIG. 18 shows a biosensor 1800 according to a further exemplary embodiment of the invention.

The biosensor 1800 according to the further exemplary embodiment corresponds essentially to the biosensor 1700 explained above and shown in FIG. 17, with the difference that no holding regions with immobilized DNA probe molecules 1709 are provided on side walls of the first branch 1701 of the second electrode 902, but rather the surface 1801 of the first branch 1701 of the second electrode 902 is covered with insulator material of the insulator layer 903 or a further insulating layer.

According to the exemplary embodiment shown in FIG. 18, holding regions on the first electrode and on the second electrode 901, 902 are consequently only on directly facing surfaces of the electrodes, i.e. on the surface 1802 of the second branch of the second electrode 902 and on the surface 1803 of the first electrode 901.

FIG. 19*a* to FIG. 19*g* represent individual method steps for producing the first electrode 901 and the second electrode 902 in the biosensors 1700, 1800.

In the insulator layer 903 as a substrate, according to the exemplary embodiment made of silicon oxide, a structure whose shape corresponds to the first electrode 901 to be formed is etched into the insulator layer 903 by using a mask layer, for example made of photoresist.

Figure 19A:
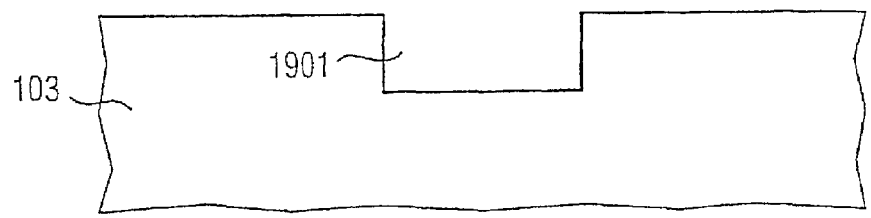
Figure 19B:
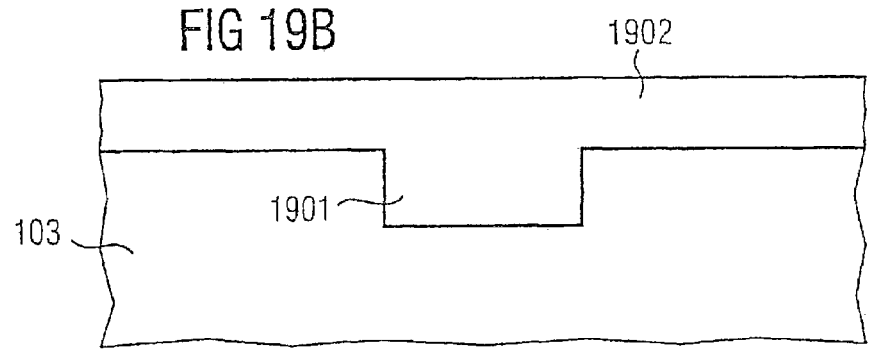

After removal of the mask layer by ashing or by a wet chemical method, a layer of the desired electrode material is applied surface-wide on the insulator layer 903, in such a way that the previously etched structure 1901 (cf. FIG. 19*a*) is at least completely filled; the structure 1901 may even be overfilled (cf. FIG. 19*b*).

Figure 19C:
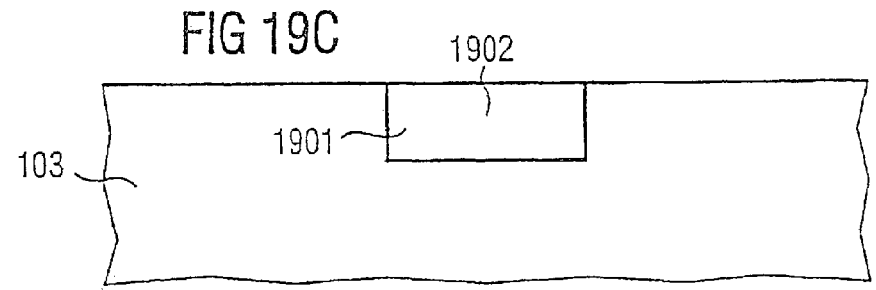

In a further step, the electrode material 1902, preferably gold, located outside the prefabricated structure 1901 is removed by means of a chemical mechanical polishing method (cf. FIG. 19*c*).

After the completion of the chemical mechanical polishing method, the first electrode 901 is therefore embedded flush in the insulator layer 903.

Electrode material 1902 outside, i.e. between the further second electrodes 902 or between the first electrodes 901, is removed without leaving any residue.

Figure 19D:
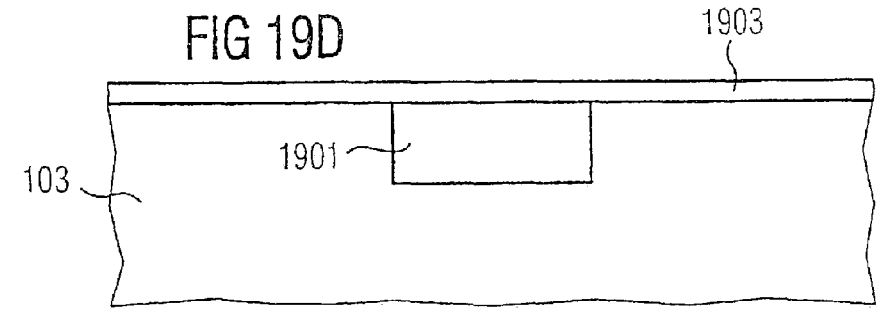

A cover layer 1903, for example made of silicon nitride, may furthermore be applied to the first electrode 901 by means of a suitable coating method, for example a CVD method, a sputtering method or an evaporation coating method (cf. FIG. 19*d*).

FIG. 19e shows several first electrodes 1901 made of gold, which are embedded next to one another in the insulator layer 903, and the cover layer 1903 located on top.

In a further stage (cf. FIG. 19f), a second electrode layer 1904 is applied on the cover layer 1903.

After masking has been completed, taking account of the desired opening between the second electrodes, which is to be formed from the second electrode layer 1904, the desired openings 1905 are formed, and the second electrode layer 1904 is etched by means of a dry etching process in a downstream plasma, in such a manner that the desired cavity 1704 is formed in accordance with the biosensors 1700, 1800 illustrated in FIG. 17 or FIG. 18 (cf. FIG. 19g).

It should be noted in this context that the cover layer 1903 is not absolutely indispensable, but it is advantageous in order to protect the first electrode 901 from superficial etching during the formation of the cavity 1704.

In an alternative embodiment, the T-shaped structure of the second electrode 902 may be formed as follows: after forming the first electrode 901 according to the method described above, a further insulator layer is formed by means of a CVD method or another suitable coating method on the first insulator layer or, if the cover layer 1903 exists, on the cover layer 1903. Subsequently, corresponding trenches are formed in the cover layer 1903, which are used to accommodate the first branch 1701 of the T-shaped structure of the second electrode 902. These trenches are filled with the electrode material gold and, according to the damascene method, the electrode material is removed which has been formed in the trenches and above the second insulator layer by means of chemical mechanical polishing, down to a predetermined height which corresponds to the height of the second branch 1702 of the T-shaped second electrode 902.

The opening 1705 between the second electrodes 902 is formed by means of photolithography, and the insulator material is subsequently removed, at least partially, by means of a dry etching method in a downstream plasma from the volume which is intended to be formed as the cavity 1704.

It should furthermore be pointed out that the embodiments described above are not restricted to an electrode whose holding region is produced by means of gold. Alternatively, electrodes made from silicon monoxide or silicon dioxide which are coated with materials in the holding regions may be used. These materials—for example known alkoxysilane derivatives—may include amine, hydroxyl, epoxy, acetoxy, isocyanate or succinimidyl ester functionalities which are able to form a covalent bond with probe molecules which are to be immobilized, in this variant in particular ligands.

The following publications are cited in this document:

[1] R. Hintsche et al., Microbiosensors Using Electrodes Made in Si-Technology, Frontiers in Biosensorics, Fundamental Aspects, edited by F. W. Scheller et al., Dirk Hauser Verlag, Basle, pp. 267-283, 1997

[2] M. Paeschke et al, Voltammetric Multichannel Measurements Using Silicon Fabricated Microelectrode Arrays, Electroanalysis, Vol. 7, No. 1, pp. 1-8, 1996

[3] R. Hintsche et al, Microbiosensors using electrodes made in Si-technology, Frontiers in Biosensorics, Fundamental Aspects, edited by F. W. Scheller et al., Birkhauser Verlag, Basle, Switzerland, 1997

[4] P. van Gerwen, Nanoscaled Interdigitated Electrode Arrays for Biochemical Sensors, IEEE, International Conference on Solid-State Sensors and Actuators, Chicago, pp. 907-910, Jun. 16-19, 1997

[5] WO 93/22678

[6] DE 19619115 A1

[7] C. Krause et al, Capacitive Detection of Surfactant Adsorption on Hydrophobized Gold Electrodes, Langmuir, Vol. 12, No. 25, pp. 6059-6064, 1996

[8] V. Mirsky et al, Capacitive Monitoring of Protein Immobilization and Antigen-Antibody Reactions on Monomolecular Alkylthiol Films on Gold Electrodes, Biosensors & Bioelectronics, Vol. 12, No. 9-10, pp. 977-989, 1997

The invention claimed is:

1. A biosensor comprising:
a first electrode device, which has a holding region for holding probe molecules which can bind macromolecular biopolymers; and
a second electrode device;
a control unit for controlling the first and the second electrode device;
wherein the first electrode device and/or the second electrode device is/are divided into a plurality of electrode segments, the electrode segments are electrically insulated from one another but can be electrically coupled to one another for adjusting the size of the effective electrode face area as a function of the electrode segments selected and coupled,
wherein the control unit controls the size of the effective electrode face area, adjusting the size of the effective electrode face area to the strength of the electrical signals from the electrode devices by coupling or decoupling the electrode segments to each other or from each other.

2. The biosensor as claimed in claim 1, having electrical switches, of which in each case one switch is coupled to an associated electrode segment in such a manner that
in a first switch position, the associated electrode segment is selected and the associated electrode segment is electrically coupled to a common connection, and that
in a second switch position, the associated electrode segment is coupled to a predetermined electrical potential and is not selected.

3. The biosensor as claimed in claim 2, having measurement electronics for measuring an electrical signal provided by the selected electrode segments, the input of the measurement electronics being electrically coupled to the selected electrode segments.

4. The biosensor as claimed in claim 3, having a switch control unit as the control unit, which is coupled to the measurement electronics, for controlling the switches, which control unit is designed in such a manner that the switches can be controlled as a function of the electrical signal recorded by the measurement electronics.

5. The biosensor as claimed in claim 1,
in which the second electrode device is divided into a plurality of electrode segments which are electrically insulated from one another, it being possible for the electrode segment for the second electrode device to be selected and electrically coupled independently of one another, so that the size of the effective electrode face area of the second electrode device can be adjusted as a function of the electrode segments selected; and
in which a non-selected electrode segment of the second electrode device is coupled to a predetermined electrical potential, in such a manner that a reduction/oxidation recycling operation can take place at the electrode device.

6. The biosensor as claimed in claim 1, further comprising:
a third electrode device, the second electrode device and the third electrode device being designed differently than the first electrode device and in such a manner that the reduction/oxidation process takes place as part of a reduction/oxidation recycling operation at the second electrode device and at the third electrode device.

7. The biosensor as claimed in claim 6,
in which a first electrical potential is applied to the first electrode device;
in which a second electrical potential is applied to the second electrode device;
in which a third electrical potential is applied to the third electrode device; and
in which the third electrical potential is selected in such a manner that during the reduction/oxidation recycling operation, the reduction or oxidation takes place only at the second electrode device and at the third electrode device.

8. The biosensor as claimed in claim 7,
in which the third electrical potential is greater than the first electrical potential; and
in which the first electrical potential is greater than the second electrical potential.

9. The biosensor as claimed in claim 1, in which the holding region of the first electrode device is coated with a material which can immobilize probe molecules.

10. The biosensor as claimed in claim 1, in which the holding region of the first electrode device is designed to hold ligands to which peptides or proteins can be bound.

11. The biosensor as claimed in claim 1, in which the holding region of the first electrode device is designed to hold DNA probe molecules to which DNA molecules can be bound.

12. The biosensor as claimed in claim 1, in which the first holding region includes at least one of the materials selected from the group consisting of hydroxyl radicals, epoxy radicals, amine radicals, acetoxy radicals, isocyanate radicals, succinimidyl ester radicals, thiol radicals, gold, silver, platinum, and titanium.

13. The biosensor as claimed in claim 6, in which the electrode devices are arranged in an interdigitated electrode device arrangement, the third electrode device being arranged between the first electrode device and the second electrode device.

14. The biosensor as claimed in claim 6, in which the first electrode device and the second electrode device and/or the third electrode device are arranged in such a manner relative to one another that substantially uncurved field lines of an electric field which is generated between the first electrode device and the second electrode device and/or the third electrode device can form between the first electrode device and the second electrode device and/or the third electrode device.

15. The biosensor as claimed in claim 6, comprising:
a multiplicity of first electrode devices which have a holding region for holding probe molecules which can bind macromolecular biopolymers;
a multiplicity of second electrode devices;
a multiplicity of third electrode devices;
the first and second electrode devices being arranged as an array; and
the second electrode devices and the third electrode devices being designed in such a manner that the reduction/oxidation process takes place as part of a reduction/oxidation recycling operation at the second electrode devices and at the third electrode devices.

16. A method for detecting macromolecular biopolymers using a biosensor, the method comprising:

providing a first electrode device, which has a holding region for holding probe molecules which can bind macromolecular biopolymers;
providing a second electrode device;
providing a control unit for controlling the first and the second electrode device;
wherein the first electrode device and/or the second electrode device is/are divided into a plurality of electrode segments, the electrode segments are electrically insulated from one another but can be electrically coupled to one another for adjusting the size of the effective electrode face area as a function of the electrode segments selected and coupled;
wherein the control unit controls the size of the effective electrode face area, adjusting the size of the effective electrode face area to the strength of the electrical signals from the electrode devices by coupling or decoupling the electrode segments to each other or from each other, providing a biosensor, the biosensor comprising:
a first electrode device, which has a holding region for holding probe molecules which can bind macromolecular biopolymers; and
a second electrode device;
a control unit for controlling the first and the second electrode device;
wherein the first electrode device and/or the second electrode device is/are divided into a plurality of electrode segments, the electrode segments are electrically insulated from one another but can be electrically coupled to one another for adjusting the size of the effective electrode face area as a function of the electrode segments selected and coupled,
wherein the control unit controls the size of the effective electrode face area, adjusting the size of the effective electrode face area to the strength of the electrical signals from the electrode devices by coupling or decoupling the electrode segments to each other or from each other;
bringing a solution which is to be analyzed into contact with the biosensor, it being possible for the solution to contain the macromolecular biopolymers which are to be recorded;
binding macromolecular biopolymers which are present in the solution which is to be analyzed to probe molecules on the first electrode device, the bound macromolecular biopolymers being marked with an enzyme;
rinsing the biosensor with a rinsing solution, so that the solution which is to be analyzed is removed;
bringing a further solution containing molecules which can be cleaved by the enzyme into contact with the biosensor;
cleaving the cleavable molecules into a first part-molecule having a first charge and a second part-molecule having a second charge;
oxidizing or reducing the first part-molecule at one of the electrode devices, generating a measurement current;
selecting and electronically coupling electrode segments of the respective electrode devices as a function of the measurement current; and
detecting the macromolecular biopolymers as a function of the measurement current.

* * * * *